United States Patent
Sprengeler et al.

(10) Patent No.: US 10,000,487 B2
(45) Date of Patent: Jun. 19, 2018

(54) HETEROCYCLIC COMPOUNDS THAT INHIBIT THE KINASE ACTIVITY OF MNK USEFUL FOR TREATING VARIOUS CANCERS

(71) Applicant: eFFECTOR Therapeutics, Inc., San Diego, CA (US)

(72) Inventors: Paul A. Sprengeler, Escondido, CA (US); Seigfried H. Reich, La Jolla, CA (US); Stephen E. Webber, San Diego, CA (US); Justin T. Ernst, San Diego, CA (US)

(73) Assignee: eFFECTOR Therapeutics, Inc., San Diego, CA (US)

(*) Notice: Subject to any disclaimer, the term of this patent is extended or adjusted under 35 U.S.C. 154(b) by 0 days. days.

(21) Appl. No.: 15/355,271

(22) Filed: Nov. 18, 2016

(65) Prior Publication Data
US 2017/0145009 A1 May 25, 2017

Related U.S. Application Data

(60) Provisional application No. 62/258,096, filed on Nov. 20, 2015.

(51) Int. Cl.
*C07D 471/04* (2006.01)
(52) U.S. Cl.
CPC .................. *C07D 471/04* (2013.01)
(58) Field of Classification Search
CPC .................................. C07D 471/04
USPC .......................................... 546/80
See application file for complete search history.

(56) References Cited

U.S. PATENT DOCUMENTS

| | | | |
|---|---|---|---|
| 5,491,144 | A | 2/1996 | Trinks et al. |
| 8,637,525 | B2 | 1/2014 | Boy et al. |
| 9,382,248 | B2 | 7/2016 | Reich et al. |
| 9,669,031 | B2 | 6/2017 | Reich et al. |
| 2007/0219218 | A1 | 9/2007 | Yu et al. |
| 2010/0105708 | A1 | 4/2010 | Jakel et al. |
| 2015/0038506 | A1 | 2/2015 | Nacro et al. |

FOREIGN PATENT DOCUMENTS

| | | |
|---|---|---|
| JP | 2009-173629 A1 | 8/2009 |
| WO | 2005082856 A2 | 9/2005 |
| WO | 2006020879 A1 | 2/2006 |
| WO | 2007021309 A1 | 2/2007 |
| WO | 2008115369 A2 | 9/2008 |
| WO | 2008117061 A2 | 10/2008 |
| WO | 2009112445 A1 | 9/2009 |
| WO | 2011106168 A1 | 1/2011 |
| WO | 2011014535 A1 | 2/2011 |
| WO | 2011017296 A1 | 2/2011 |
| WO | 2012041987 A1 | 4/2012 |
| WO | 2012075140 A1 | 6/2012 |

(Continued)

OTHER PUBLICATIONS

Venkatesh et al., J. Pharm. Sci. 89, 145-54 (2000) (p. 146, left column).*
Apr. 12, 2017 Written Opinion and International Search Report Issued in International Patent Application No. PCT/US2016/062787.
Aurora Fine Chemicals, Jan. 5, 2014 Chemical Catalog excerpt 1511646-58-4.
Aurora Fine Chemicals, Dec. 29, 2013 Chemical Catalog excerpt 1505663-52-4.
Aurora Fine Chemicals, Dec. 17, 2013 Chemical Catalog excerpt 1496979-81-7.
Aurora Fine Chemicals, Dec. 1, 2013 Chemical Catalog excerpt 1484631-21-1.
Aurora Fine Chemicals, Nov. 26, 2013 Chemical Catalog excerpt 1481116-61-3.
U.S. Appl. No. 15/611,966, filed Jun. 2, 2017 in the name of eFFECTOR Therapeutics, Inc.
U.S. Appl. No. 15/337,237, filed Oct. 28, 2016 in the name of eFFECTOR Therapeutics, Inc.
U.S. Appl. No. 15/130,538, filed Apr. 15, 2016 in the name of eFFECTOR Therapeutics, Inc.

(Continued)

*Primary Examiner* — Nizal S Chandrakumar
(74) *Attorney, Agent, or Firm* — Mintz, Levin, Cohn, Ferris, Glovsky and Popeo, P.C.

(57) ABSTRACT

The present invention provides synthesis, pharmaceutically acceptable formulations and uses of compounds in accordance with Formula IA or Formula IB, as well as stereoisomers, tautomers or pharmaceutically acceptable salts thereof.

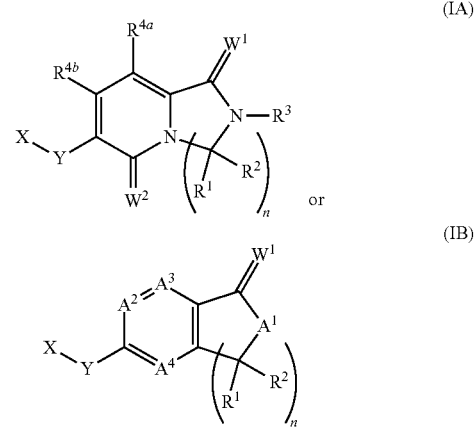

For Formula IA and Formula IB compounds $A^1$, $A^2$, $A^3$, $A^4$, $W^1$, $W^2$, Y, X, $R^1$, $R^2$, $R^3$, $R^{4a}$, $R^{4b}$, $R^{5a}$, $R^{5b}$, $R^6$, $R^7$, $R^8$, $R^9$, $R^{9a}$, $R^{9b}$, $R^{10}$ and subscript n are as defined in the specification. The inventive Formula IA and Formula IB compounds are inhibitors of Mnk and find utility in any number of therapeutic applications, including but not limited to treatment of inflammation and various cancers.

5 Claims, No Drawings

(56) References Cited

FOREIGN PATENT DOCUMENTS

| WO | 2013000994 A1 | 1/2013 |
|---|---|---|
| WO | 2013043192 A1 | 3/2013 |
| WO | 2013100632 A1 | 4/2013 |
| WO | 2013147711 A1 | 10/2013 |
| WO | 2013148748 A1 | 10/2013 |
| WO | 2013151975 A1 | 10/2013 |
| WO | 2014044691 A1 | 3/2014 |
| WO | 2014088519 A1 | 6/2014 |
| WO | 2014099941 A1 | 6/2014 |
| WO | 2014128093 A1 | 8/2014 |
| WO | 2015074986 A1 | 5/2015 |

OTHER PUBLICATIONS

U.S. Appl. No. 15/337,184, filed Oct. 28, 2016 in the name of eFFECTOR Therapeutics, Inc.

Oyarzabal, Julen et al., "Discovery of Mitogen-Activated Protein Kinase-Interacting Kinase 1 Inhibitors by a Comprehensive Fragment-Oriented Virtual Screening Approach" Journal of Medicinal Chemistry, 2010, vol. 53, No. 18, 6618-6628.

Yu et al., "Discovery of 4-(dihydropyridinon-3-yl)amino-5-methylthieno[2,3-d] pyrimidine derivatives as potent Mnk inhibitors: synthesis, structureeactivity relationship analysis and biological evaluation" European Journal of Medicinal Chemistry, May 5, 2015, vol. 95, 116-126.

Teo et al., "An integrated approach for discovery of highly potent and selective Mnk inhibitors: Screening, synthesis and SAR analysis" European Journal of Medicinal Chemistry, Sep. 2015, vol. 103, 539-550.

\* cited by examiner

HETEROCYCLIC COMPOUNDS THAT INHIBIT THE KINASE ACTIVITY OF MNK USEFUL FOR TREATING VARIOUS CANCERS

The present application claims the benefit of U.S. provisional application No. 62/258,096, filed Nov. 20, 2015, which is herein incorporated by reference in its entirety.

FIELD

The present invention generally relates to compounds having activity as inhibitors of MAP kinase interacting kinase (Mnk), for example Mnk1 and Mnk2, as well as to related compositions and methods for utilizing the inventive compounds as therapeutic agents for treatment of Mnk dependent diseases, including the treatment of cancer.

BACKGROUND

Eukaryotic initiation factor 4E (eIF4E) is a general translation factor, but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

Initiation of cap-dependent translation is thought to depend on the assembly of eIF4F, an initiation factor complex including eIF4E, the scaffold protein eIF4G, and the RNA helicase eIF4A. Because eIF4E is the only one of these proteins that binds directly to the mRNA cap structure, it is the key factor for the assembly of eIF4F at the 5' cap. The scaffold protein, eIF4G, also recruits the 40S ribosomal subunit to the mRNA via its interaction with eIF3 and binds eIF4B, a protein that aids the RNA-helicase function of eIF4A, thus facilitating the translation of mRNAs that contain structured 5'-UTRs. The availability of eIF4E as part of the eIF4F complex is a limiting factor in controlling the rate of translation, and therefore eIF4E is an important regulator of mRNA translation.

Regulation of eIF4E activity forms a node of convergence of the PI3K/Akt/mTOR and Ras/Raf/MAPK signaling pathways. The PI3K (phosphoinositide 3-kinase)/PTEN (phosphatase and tensin homologue deleted on chromosome ten)/Akt/mTOR (mammalian target of rapamycin) pathway is often involved in tumorgenesis and in sensitivity and resistance to cancer therapy. Deregulated signaling through the PI3K/PTEN/Akt/mTOR pathway is often the result of genetic alterations in critical components of this pathway and/or mutations at upstream growth factor receptors or signaling components. PI3K initiates a cascade of events when activated by, for example, extracellular growth factors, mitogens, cytokines and/or receptors, PDK1 activates Akt, which in turn phosphorylates and inactivates the tumor suppressor complex comprising TSC1 and 2 (tuberous sclerosis complex 1/2), resulting in the activation of mTORC1 (target of rapamycin complex 1) by Rheb-GTP. Activation of PDK1 and Akt by PI3Ks is negatively regulated by PTEN.

PTEN is a critical tumor suppressor gene and is often mutated or silenced in human cancers. Its loss results in activation of Akt and increases downstream mTORC1 signaling. The involvement of mTOR complex1 (mTORC1) in neoplastic transformation appears to depend on its regulatory role toward the eIF4F complex; overexpression of eIF4E can confer resistance to rapamycin. mTORC1 regulates the eIF4F complex assembly that is critical for the translation of mRNAs associated with cell growth, prevention of apoptosis and transformation. mTORC1 achieves this by phosphorylation and inactivation of 4E-BPs and the subsequent dissociation of 4E-BPs from eIF4E. This then enables eIF4E to interact with the scaffold protein eIF4G, permitting assembly of the eIF4F complex for the translation of structured mRNAs. mTORC1 also promotes activation of the translational activator, S6K, which phosphorylates the ribosomal protein S6 and other substrates, including eIF4B. mTORC1 signaling is inhibited by rapamycin and its analogues (rapalogs), although these compounds act allosterically, rather than directly inhibiting mTOR kinase activity.

Given the importance of the PI3K/Akt/mTOR pathway in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt. It has been shown that prolonged treatment of cancer cells or patients with mTOR inhibitors causes elevated PI3K activity that leads to phosphorylation of Akt and eIF4E, and promotes cancer cell survival. eIF4E, acting downstream of Akt and mTOR, recapitulates Akt's action in tumorigenesis and drug resistance, and Akt signaling via eIF4E is an important mechanism of oncogenesis and drug resistance in vivo.

In addition to the PI3K/Akt/mTOR pathway, eIF4E is also the target of the Ras/Raf/MAP signaling cascade which is activated by growth factors and for the stress-activated p38 MAP kinase pathway. Erk1/2 and p38 then phosphorylate MAP kinase-interacting kinase 1 (Mnk1) and MAP kinase-interacting kinase 2 (Mnk2). The Erk pathway is also activated in many cancers, reflecting, for example, activating mutations in Ras (found in around 20% of tumors) or loss of function of the Ras GTPase-activator protein NF1. Mnk1 and Mnk2 are threonine/serine protein kinases and specifically phosphorylate serine 209 (Ser209) of eIF4E within the eIF4F complex, by virtue of the interaction between eIF4E and the Mnks, which serves to recruit Mnks to act on eIF4E. Mice with mutated eIF4E, in which Ser209 is replaced by alanine, shows no eIF4E phosphorylation and significantly attenuated tumor growth. Significantly, while Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088 (Tschopp et al., *Mol Cell Biol Res Commun.* 3(4):205-211, 2000); CGP57380 (Rowlett et al., *Am J Physiol Gastrointest Liver Physiol.* 294(2):G452-459, 2008); and Cercosporamide (Konicek et al., *Cancer Res.* 71(5):1849-1857, 2011).

These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in WO 2014/044691 and the various patent documents cited therein and the 4-(dihydropyridinon-3-yl)amino-5-methylthieno[2,3,-d]pyrimidines disclosed by Yu et al., *European Journal of Med. Chem.*, 95: 116-126, 2015.

Accordingly, while advances have been made in this field there remains a significant need in the art for compounds that specifically inhibit Mnk kinase activity, particularly with regard to Mnk's role in regulation of cancer pathways, as well as for associated composition and methods. The present invention fulfills this need and provides further related advantages.

SUMMARY

The present invention is directed to compounds that inhibit or modulate the activity of Mnk, as well as stereoisomers, tautomers and pharmaceutically acceptable salts of such compounds. The invention also is directed to pharmaceutically acceptable compositions containing such compounds and associated methods for treating conditions that would benefit from Mnk inhibition, such as cancer.

In one embodiment the invention is directed to compounds according to Formula IA or Formula IB as well as to a stereoisomer, tautomer or pharmaceutically acceptable salt of such compounds,

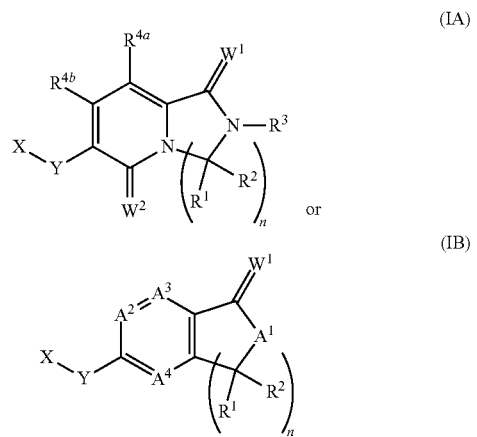

wherein
$A^1$ is —$NR^5$ or —$CR^{5a}R^{5b}$;
$A^2$ is —N— or —$CR^6$;
$A^3$ is —N— or —$CR^7$;
$A^4$ is —N— or —$CR^8$;
$W^1$ and $W^2$ independently are O, S, NH, NO($R^9$) or $CR^{9a}R^{9b}$;
Y is —O—, —S—, —C(O)—, —$NR^8$, —S=O, —$S(O)_2$, —CH(OH), —$CH_2$— or —CH[($C_1$-$C_4$)alkyl];
n is 1, 2 or 3;
$R^1$ and $R^2$ independently are —H, —$NHR^{10}$, $NHR^{10}$-alkylene, ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene or heteroarylalkylene, wherein in Formula IB at least one of $R^1$ or $R^2$ is not —H; or $R^1$ and $R^2$ together with the carbon atom to which they are attached form a cycloalkyl or heterocyclyl ring;
$R^3$ is hydrogen, lower alkyl, cycloalkyl, heterocyclyl, aryl or heterocyclyl;
$R^{4a}$ and $R^{4b}$ independently are hydrogen, halogen, hydroxyl, thiol, hydroxyalkylene, cyano, —($C_1$-$C_8$)alkyl, —O($C_1$-$C_8$)alkyl, acyl, thioalkyl, —($C_2$-$C_8$)alkenyl, —($C_2$-$C_8$)alkynyl, cycloalkyl, aryl or heterocyclyl;
$R^5$ is —H, —OH, acetyl, —($C_1$-$C_8$)alkyl, —C(O)alkyl, —C(O)cycloalkyl, —C(O)O—($C_1$-$C_8$)alkyl, cycloalkyl, aryl, heteroaryl or heterocyclyl;
$R^{5a}$ and $R^{5b}$ independently are —H, —OH, acetyl, —($C_1$-$C_8$)alkyl, —O($C_1$-$C_8$)alkyl, —C(O)alkyl, —C(O)cycloalkyl, —C(O)O—($C_1$-$C_8$)alkyl, cycloalkyl, aryl, heteroaryl or heterocyclyl;
$R^6$ is —H, —OH, halogen, —CN, acetyl, —($C_1$-$C_8$)alkyl, —S($C_1$-$C_8$)alkyl, —($C_2$-$C_8$)alkenyl, —($C_2$-$C_8$)alkynyl, —O($C_1$-$C_8$)alkyl, ($C_1$-$C_8$)haloalkyl, —$NHR^{10}$, —$NR^{10}R^{10}$, $NHR^{10}$-alkylene, $NR^{10}R^{10}$-alkylene or —O($C_1$-$C_8$)haloalkyl;
$R^7$ is —H, —OH, —SH, —CN, —$S(O)_2R^{10}$, halogen, —S($C_1$-$C_8$)alkyl, —$NHR^{10}$, —$NR^{10}R^{10}$, ($C_1$-$C_8$)alkyl, ($C_2$-$C_8$)alkenyl, ($C_2$-$C_8$)alkynyl, ($C_1$-$C_8$)haloalkyl, —O($C_1$-$C_8$)haloalkyl, —O($C_1$-$C_8$)alkyl, —O($C_1$-$C_8$)alkyleneNHR$^{10}$, —O($C_1$-$C_8$)alkyleneNR$^{10}$R$^{10}$, —($C_1$-$C_8$)alkyleneNHR$^{10}$, —($C_1$-$C_8$)alkyleneNR$^{10}$R$^{10}$, —S($C_1$-$C_8$)alkyl, cycloalkyl, heterocyclyl, heteroaryl or aryl;
$R^8$ is —H, —OH, —CN, —$SR^{10}$, halogen, —C(O)[($C_1$-$C_8$)alkyl], —$S(O)_2(C_1$-$C_8)$ alkyl, —C(O)NHR$^{10}$, —C(O)NR$^{10}$R$^{10}$, —NHR$^{10}$, —NR$^{10}$R$^{10}$, NHR$^{10}$-alkylene, NR$^{10}$R$^{10}$-alkylene, ($C_1$-$C_8$)alkyl, ($C_2$-$C_8$)alkenyl, ($C_2$-$C_8$)alkynyl, ($C_1$-$C_8$)haloalkyl, —O($C_1$-$C_8$)alkyl, —O($C_1$-$C_8$)haloalkyl, —O($C_1$-$C_8$)alkyleneNHR$^{10}$, —O($C_1$-$C_8$)alkyleneNR$^{10}$R$^{10}$, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl or heterocyclylaminyl;
$R^9$, $R^{9a}$ and $R^{9b}$ are independently —H, ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene or heteroarylalkylene, or
$R^{9a}$ and $R^{9b}$ together with the carbon atom to which they are attached form a cycloalkyl or heterocyclyl ring;
$R^{10}$ is —H, —OH, —C(O)O($C_1$-$C_8$)alkyl, —C(O)($C_1$-$C_8$)alkyl, —C(O)—NH$_2$, —C(O)—NH($C_1$-$C_8$)alkyl, NH$_2$—C(O)-alkylene, —S($C_1$-$C_8$)alkyl, acetyl, —($C_1$-$C_8$) alkyl, ($C_2$-$C_8$)alkenyl, ($C_2$-$C_8$)alkynyl, —O($C_1$-$C_8$)alkyl, ($C_1$-$C_8$) haloalkyl, alkylcarbonylaminyl, alkylaminyl, —C(O)alkyl, —C(O)cycloalkyl, —C(O)O—($C_1$-$C_8$)alkyl, aryl, heteroaryl, heterocyclyl or cycloalkyl;
X is selected from the following table;

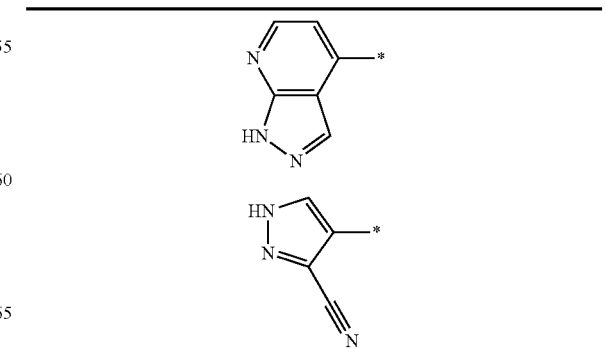

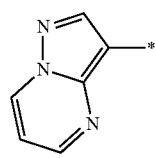 [SMILES: *c1cnn2cccnc12]
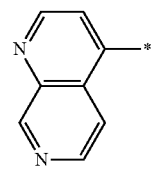 [SMILES: *c1ccnc2cnccc12]
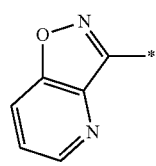 [SMILES: *c1noc2cccnc12]
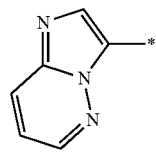 [SMILES: *c1cnc2cccnn12]
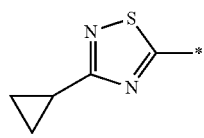 [SMILES: *c1nc(C2CC2)ns1]
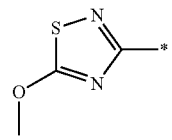 [SMILES: *c1nsc(OC)n1]
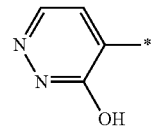 [SMILES: *c1ccnnc1O]
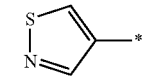 [SMILES: *c1cnsc1]
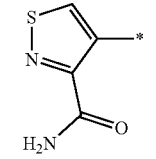 [SMILES: *c1csnc1C(N)=O]
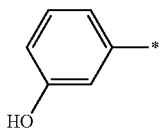 [SMILES: *c1cccc(O)c1]
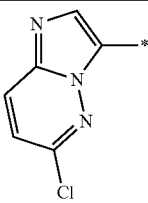
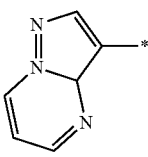
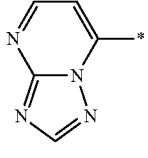 [SMILES: *c1ccnc2ncnn12]
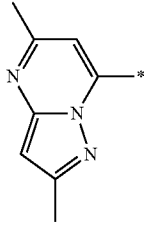 [SMILES: *c1cc(C)nc2cc(C)nn12]
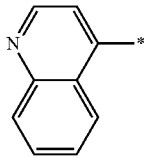 [SMILES: *c1ccnc2ccccc12]
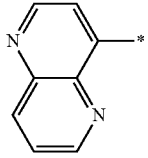 [SMILES: *c1ccnc2cccnc12]
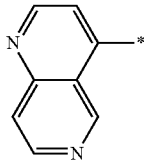 [SMILES: *c1ccnc2ccncc12]
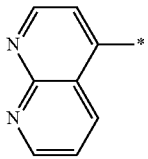 [SMILES: *c1ccnc2ncccc12]
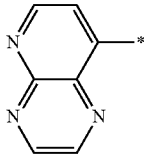 [SMILES: *c1ccnc2nccnc12]

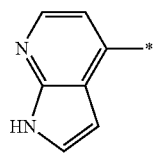 [SMILES: *c1ccnc2[nH]ccc12]
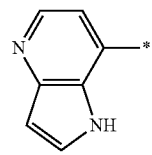 [SMILES: *c1ccnc2cc[nH]c12]
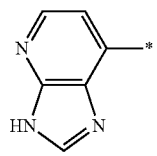 [SMILES: *c1ccnc2[nH]cnc12]
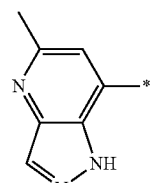
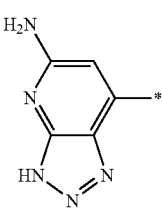 [SMILES: *c1cc(N)nc2[nH]nnc12]
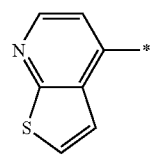 [SMILES: *c1ccnc2sccc12]
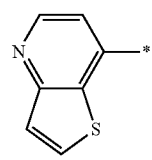 [SMILES: *c1ccnc2ccsc12]
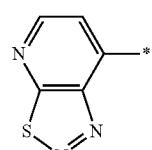
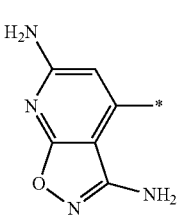 [SMILES: *c1cc(N)nc2onc(N)c12]
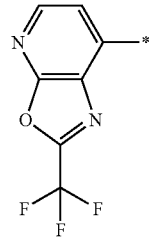 [SMILES: *c1ccnc2oc(C(F)(F)F)nc12]
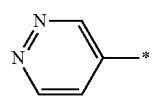
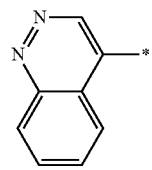 [SMILES: *c1cnnc2ccccc12]
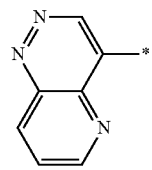 [SMILES: *c1cnnc2cccnc12]
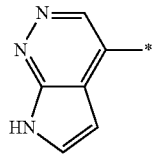
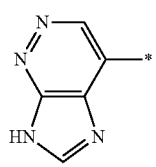 [SMILES: *c1cnnc2[nH]cnc12]
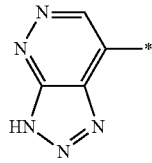 [SMILES: *c1cnnc2[nH]nnc12]
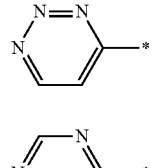
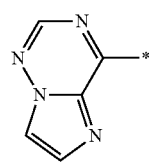

-continued
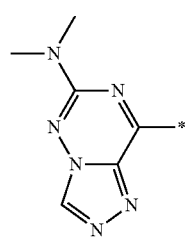 [SMILES: *c1nc(N(C)C)nn2cnnc12]
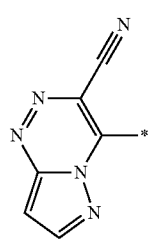
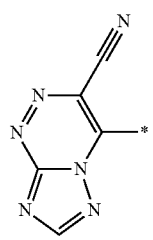
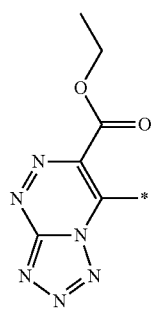 [SMILES: *c1c(C(=O)OCC)nnc2nnnn12]
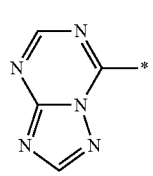 [SMILES: *c1ncnc2ncnn12]
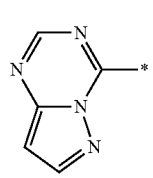 [SMILES: *c1ncnc2ccnn12]
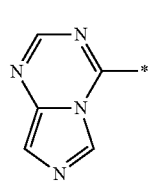 [SMILES: *c1ncnc2cncn12]
-continued
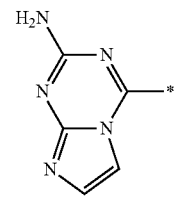
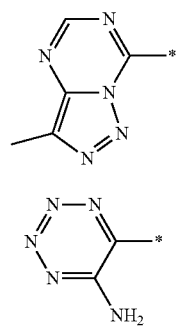
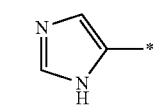
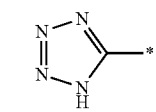 [SMILES: *c1nnn[nH]1]
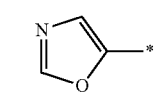
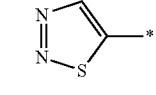
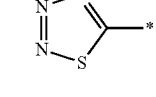
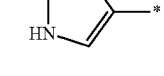
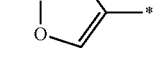
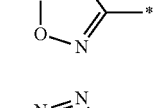
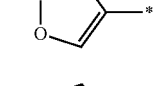
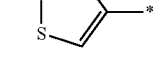

-continued
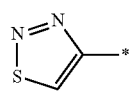
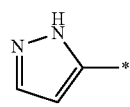
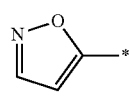
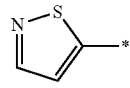 [SMILES: *c1ccns1]
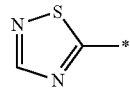
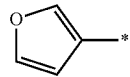 [SMILES: *c1ccoc1]
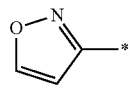
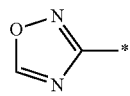
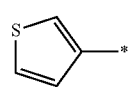 [SMILES: *c1ccsc1]
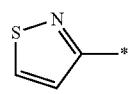
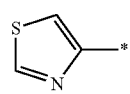
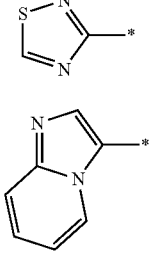
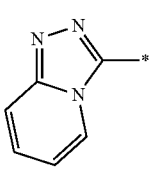 [SMILES: *c1nnc2ccccn12]
-continued
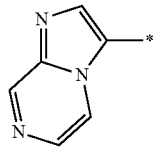 [SMILES: *c1cnc2cnccn12]
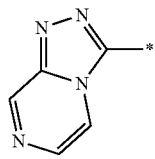 [SMILES: *c1nnc2cnccn12]
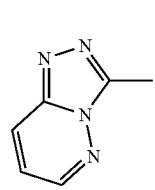
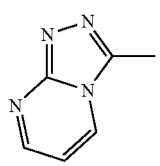
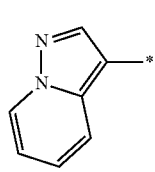 [SMILES: *c1cnn2ccccc12]
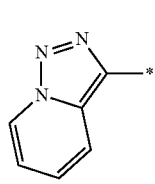 [SMILES: *c1nnn2ccccc12]
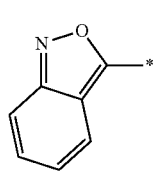 [SMILES: *c1onc2ccccc12]
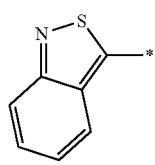 [SMILES: *c1snc2ccccc12]
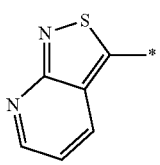 [SMILES: *c1snc2ncccc12]

13
-continued
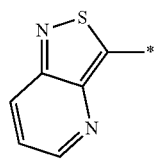 [SMILES: *c1snc2cccnc12]
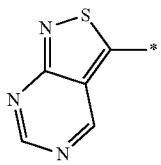
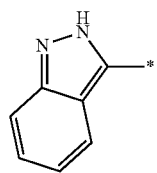 [SMILES: *c1[nH]nc2ccccc12]
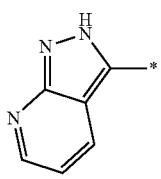
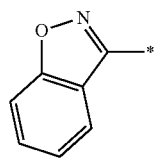 [SMILES: *c1noc2ccccc12]
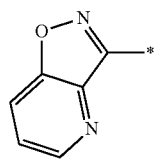 [SMILES: *c1noc2cccnc12]
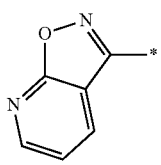
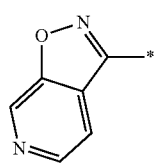 [SMILES: *c1noc2cnccc12]
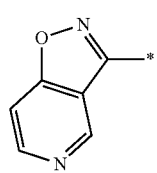 [SMILES: *c1noc2ccncc12]
14
-continued
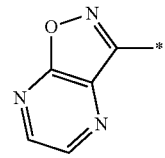 [SMILES: *c1noc2nccnc12]
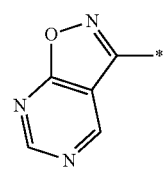 [SMILES: *c1noc2ncncc12]
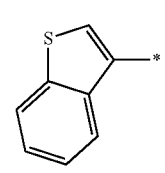 [SMILES: *c1csc2ccccc12]
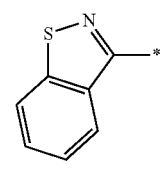 [SMILES: *c1nsc2ccccc12]
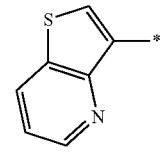 [SMILES: *c1csc2cccnc12]
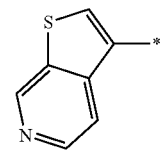 [SMILES: *c1csc2cnccc12]
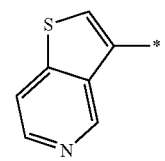 [SMILES: *c1csc2ccncc12]
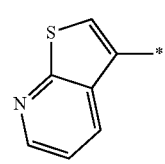 [SMILES: *c1csc2ncccc12]
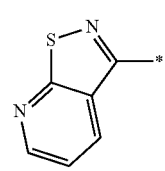 [SMILES: *c1nsc2ncccc12]

-continued
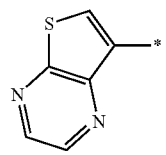
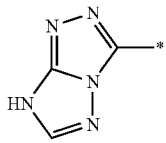
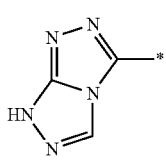 [SMILES: *c1nnc2[nH]ncn12]
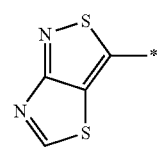 [SMILES: *c1snc2ncsc12]
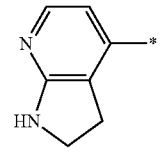
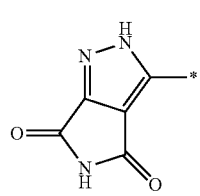 [SMILES: *c1[nH]nc2c1C(=O)NC2=O]
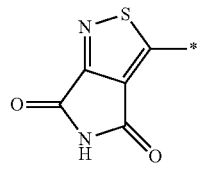 [SMILES: *c1snc2c1C(=O)NC2=O]
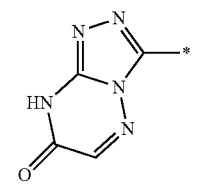 [SMILES: *c1nnc2[nH]c(=O)cnn12]
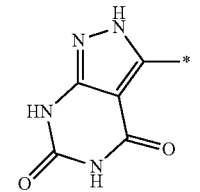 [SMILES: *c1[nH]nc2[nH]c(=O)[nH]c(=O)c12]
-continued
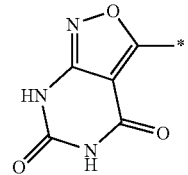 [SMILES: *c1onc2[nH]c(=O)[nH]c(=O)c12]
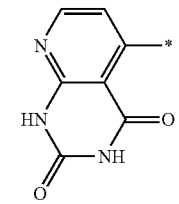 [SMILES: *c1ccnc2[nH]c(=O)[nH]c(=O)c12]
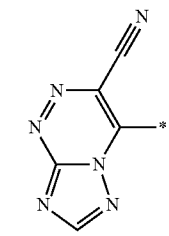 [SMILES: *c1c(C#N)nnc2ncnn12]
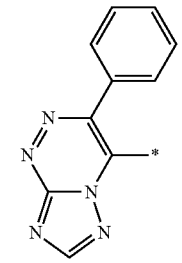 [SMILES: *c1c(-c2ccccc2)nnc2ncnn12]
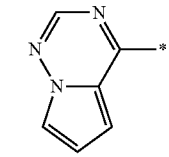 [SMILES: *c1ncnn2cccc12]
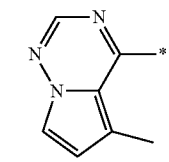 [SMILES: *c1ncnn2ccc(C)c12]
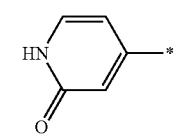
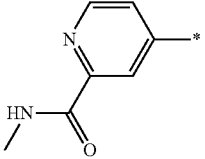 [SMILES: *c1ccnc(C(=O)NC)c1]

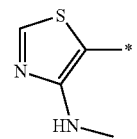
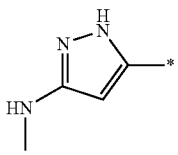
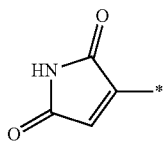 [SMILES: *C1=CC(=O)NC1=O]
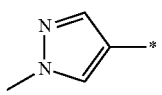
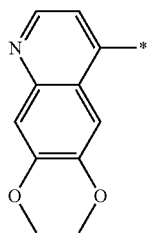 [SMILES: *c1ccnc2cc(OC)c(OC)cc12]
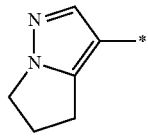 [SMILES: *c1cnn2c1CCC2]
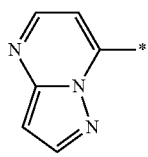 [SMILES: *c1ccnc2ccnn12]
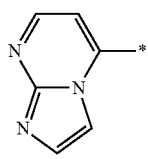 [SMILES: *c1ccnc2nccn12]
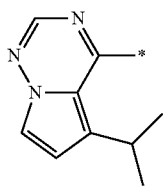 [SMILES: *c1ncnn2ccc(C(C)C)c12]

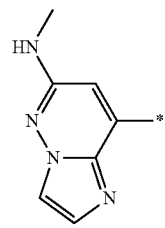 [SMILES: *c1cc(NC)nn2ccnc12]
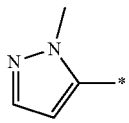 [SMILES: *c1ccnn1C]
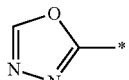
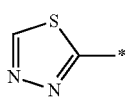

wherein * indicates the point of attachment of variable "X" to variable "Y"; and wherein any alkyl, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl is optionally substituted with 1, 2, or 3 groups selected from —OH, —CN, —SH, —S(O)NH$_2$, —S(O) NH$_2$, halogen, —NH$_2$, oxo, —NH(C$_1$-C$_4$)alkyl, —N[(C$_1$-C$_4$)alkyl]$_2$, —C(O)NH$_2$, —COOH, —COOMe, acetyl, —(C$_1$-C$_8$)alkyl, —O(C$_1$-C$_8$)alkyl (C$_2$-C$_8$)alkenyl, (C$_2$-C$_8$) alkynyl, haloalkyl, thioalkyl, cyanomethylene, alkylaminyl, NH$_2$—C(O)-alkylene, NH$_2$—C(O)-alkylene, —NH(Me)-C (O)-alkylene, —CH$_2$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$_2$—C(O)-cycloalkyl, —C(O)-cycloalkyl, —CH$_2$—C(O)-aryl, —CH$_2$-aryl, —C(O)-aryl, —CH$_2$—C(O)-heterocycloalkyl, —C(O)-heterocycloalkyl, heterocyclylaminyl or heterocyclyl.

The present invention also provides a pharmaceutical composition comprising (i) a therapeutically effective amount of at least one compound according to Formula IA or Formula IB or stereoisomers, tautomers or pharmaceutically acceptable salts thereof; (ii) in combination with a pharmaceutically acceptable carrier, diluent or excipient.

Also provided by the present invention is a method for attenuating or inhibiting the activity of MnK in at least one cell overexpressing Mnk, comprising contacting the at least one cell with a compound according to Formula IA or Formula IB or a stereoisomer, tautomer or pharmaceutically acceptable salt thereof.

According to the inventive method at least one cell is a colon cancer cell, a gastric cancer cell, a thyroid cancer cell, a lung cancer cell, a leukemia cell, a B-cell lymphoma, a T-cell lymphoma, a hairy cell lymphoma, Hodgkin's lymphoma cell, non-Hodgkin's lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

According to yet another embodiment the invention provides a method for treating a Mnk dependent condition in a mammal in need thereof, comprising administering to the mammal (i) a therapeutically effective amount of at least one compound according to Formula IA or Formula IB or a stereoisomer, tautomer or pharmaceutically acceptable salt thereof, or (ii) a pharmaceutical composition in accordance with the invention.

Compounds and pharmaceutically acceptable formulations in accordance with the invention are useful for treating an Mnk dependent condition such as colon cancer, colorectal, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple melanoma, brain cancer, CNS cancer, renal cancer, prostate cancer, ovarian cancer, or breast cancer.

The above embodiments and other aspects of the invention are readily apparent in the detailed description that follows. Various references are set forth herein which describe in more detail certain background information, procedures, compounds and/or compositions, and are each hereby incorporated by reference in their entirety.

DETAILED DESCRIPTION

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

"Amino" refers to the —NH$_2$ substituent.

"Aminocarbonyl" refers to the —C(O)NH$_2$ substituent.

"Carboxyl" refers to the —CO$_2$H substituent.

"Carbonyl" refers to a —C(O)— or —C(=O)— group. Both notations are used interchangeably within the specification.

"Cyano" refers to the —C≡N substituent.

"Cyanoalkylene" refers to the -(alkylene)C≡N substituent.

"Acetyl" refers to the —C(O)CH$_3$ substituent.

"Hydroxy" or "hydroxyl" refers to the —OH substituent.

"Hydroxyalkylene" refers to the -(alkylene)OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —OR$_a$ where R$_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Alkylaminyl" refers to a radical of the formula —NHR$_a$ or —NR$_a$R$_a$ where each R$_a$ is, independently, an alkyl radical having the indicated number of carbon atoms as defined above.

"Cycloalkylaminyl" refers to a radical of the formula —NHR$_a$ where R$_a$ is a cycloalkyl radical as defined herein.

"Alkylcarbonylaminyl" refers to a radical of the formula —NHC(O)R$_a$, where R$_a$ is an alkyl radical having the indicated number of carbon atoms as defined herein.

"Cycloalkylcarbonylaminyl" refers to a radical of the formula —NHC(O)R$_a$, where R$_a$ is a cycloalkyl radical as defined herein.

"Alkylaminocarbonyl" refers to a radical of the formula —C(O)NHR$_a$ or —C(O)NR$_a$R$_a$, where each R$_a$ is independently, an alkyl radical having the indicated number of carbon atoms as defined herein.

"Cyclolkylaminocarbonyl" refers to a radical of the formula —C(O)NHR$_a$, where R$_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to a aryl group or a substituted aryl group.

"Arylene" denotes divalent aryl, and "substituted arylene" refers to divalent substituted aryl.

"Aralkyl" or "aralkylene" may be used interchangeably and refer to a radical of the formula —R$_b$—R$_c$ where R$_b$ is an alkylene chain as defined herein and R$_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Cycloalkylalkylene" or "cycloalkylalkyl" may be used interchangeably and refer to a radical of the formula —R$_b$R$_e$, where R$_b$ is an alkylene chain as defined herein and R$_e$ is a cycloalkyl radical as defined herein. In certain embodiments, R$_b$ is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —R$_b$R$_f$ where R$_b$ is an alkylene chain as defined herein and R$_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_bR_g$ where $R_b$ is an alkylene chain as defined above and $R_g$ is a heteroaryl radical as defined above.

"Thioalkyl" refers to a radical of the formula —$SR_a$ where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— group in which a hexavalent sulfur is attached to each of the two oxygen atoms through double bonds and is further attached to two carbon atoms through single covalent bonds.

The term "oxime" refers to a —$C(R_a)$=N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:
(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The terms "modulate", "modulation" and the like refer to the ability of a compound to increase or decrease the function, or activity of, for example, MAP kinase interacting kinase (Mnk). "Modulation", in its various forms, is intended to encompass inhibition, antagonism, partial antagonism, activation, agonism and/or partial agonism of the activity associated with Mnk. Mnk inhibitors are compounds that bind to, partially or totally block stimulation, decrease, prevent, delay activation, inactivate, desensitize, or down regulate signal transduction. The ability of a compound to modulate Mnk activity can be demonstrated in an enzymatic assay or a cell-based assay.

A "patient" or "subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Exemplary prodrugs of compounds in accordance with Formula IA or Formula IB are esters, acetamides, and amides.

Compounds of the Invention

The present invention generally is directed to compounds encompassed by the genus of Formula IA or Formula IB, as well as stereoisomers, tautomers or pharmaceutically acceptable salts thereof.

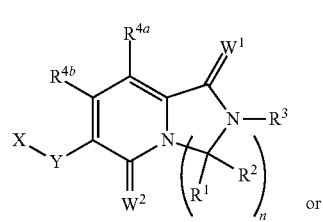

(IA)

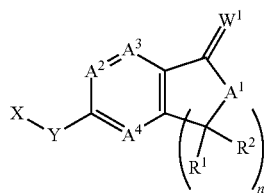

(IB)

For Formula IA and Formula IB compounds $A^1$, $A^2$, $A^3$, $A^4$, $W^1$, $W^2$, $R^1$, $R^2$, $R^3$, $R^{4a}$, $R^{4b}$, $R^5$, $R^{5a}$, $R^{5b}$, $R^6$, $R^7$, $R^8$, $R^9$, $R^{9a}$, $R^{9b}$, $R^{10}$, X, Y and subscript "n" are as defined in the specification. Described below, however, are specific embodiments of Formula IA compounds and Formula IB compounds.

In one embodiment $A^1$ is —$NR^5$. In another embodiment $A^1$ is —NH or —N(alkyl).

In one embodiment $A^1$ is —$CH_2$.

In one embodiment $A^2$ is —$CR^6$. In another embodiment $A^2$ is —CH or —C(Me).

In one embodiment $A^2$ is —N.

In one embodiment $A^3$ is —$CR^7$.

In one embodiment $A^4$ is —$CR^8$.

In one embodiment the invention provides Formula IA and IB compounds where $W^1$ and $W^2$ in independently are O and Y is —NH.

In one embodiment subscript "n" is 1.

In one embodiment at least one of $R^1$ and $R^2$ is ($C_1$-$C_8$) alkyl, —$NHR^{10}$ or $NHR^{10}$-alkylene. In another embodiment at least one of $R^1$ and $R^2$ is methyl, ethyl, propyl, isopropyl, butyl, sec-butyl, t-butyl, isobutyl, pentyl or hexyl.

In one embodiment at least one of $R^1$ or $R^2$ is $NH_2$ or —$NH_2$-alkylene. In another embodiment at least one of $R^1$ or $R^2$ is an aminomethylene.

In one embodiment at least one of $R^1$ or $R^2$ is a halogen substituted ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene or heteroarylalkylene.

In one embodiment at least one of $R^1$ or $R^2$ is an optionally substituted heteroaryl. In another embodiment the heteroaryl is a thiophene.

In one embodiment $R^1$ and $R^2$ are hydrogen for compounds of Formula IA.

In one embodiment $R^1$ and $R^2$ together with the respective carbon atom to which they are attached form a fused cycloalkyl ring. In another embodiment the cycloalkyl is cyclobutyl, cyclopentyl, cyclohexyl, 2,2-dimethylcyclobutyl, 4-aminocyclohexyl, 4-methylcyclohexyl, 4-ethylcyclohexyl, 2,2-difluoroethyl-4-cyclohexyl, 4,4-difluorocyclohexy, 4-cyanocyclohexyl, 4-trifluoromethylcyclohexyl, 4-hydroxycyclohexyl, 3-hydroxycyclopently, 3-aminocyclopentyl or 3-methylcyclopentyl ring systems. In yet another embodiment the cycloalkyl is cyclobutyl, cyclopentyl or cyclohexyl.

In one embodiment $R^1$ and $R^2$ together with the respective carbon atom to which they are attached form a fused heterocyclyl. In another embodiment the heterocyclyl is piperidine, 1-(2,2-difluorethylpiperidine), N-methylpiperidine, tetrahydropyran or pyrrolidine.

In one embodiment $R^{4a}$ and $R^{4b}$ in Formula IA independently are —H, —OH, —F, —Cl, —($C_1$-$C_8$)haloalkyl, methyl or ethyl.

In one embodiment $R^5$, $R^{5a}$ and $R^{5b}$ are hydrogen.

In one embodiment $R^6$ is —H, —OH, halogen, —CN, acetyl or —($C_1$-$C_8$)alkyl. In another embodiment $R^6$ is methyl, ethyl, propyl or butyl. In yet another embodiment $R^6$ is —H.

In one embodiment $R^7$ is —H, —OH, —SH, —CN, -halogen or —$NHR^{10}$.

In one embodiment $R^7$ is methyl or ethyl.

In one embodiment $R^7$ is a —($C_1$-$C_8$)haloalkyl. In one embodiment $R^7$ is —$CHF_2$ or —$CF_3$.

In one embodiment $R^7$ is —O($C_1$-$C_8$)alkyl. In another embodiment $R^7$ is —OMe or —OEt.

In one embodiment $R^8$ is —H, —OH, —CN, —Cl, —F or —($C_1$-$C_8$)alkyl. In another embodiment $R^8$ is methyl, ethyl or propyl. In yet another embodiment $R^8$ is —H.

In one embodiment $R^8$ is $NH_2$—($C_1$-$C_8$)alkylene. In another embodiment $R^8$ is —$NH_2$ methylene or —$NH_2$-ethylene.

In one embodiment $R^8$ is —O($C_1$-$C_8$)alkyl or —($C_1$-$C_8$) haloalkyl. In another embodiment $R^8$ is —OMe and —OEt. In yet another embodiment $R^8$ is —$CHF_2$, —$CH_2Cl$ or —$CF_3$.

In one embodiment $R^8$ is —C(O)($C_1$-$C_8$)alkyl. In another embodiment $R^8$ is —C(O)methyl or —C(O)ethyl.

In one embodiment $R^9$, $R^{9a}$ and $R^{9b}$ are independently —H or —($C_1$-$C_8$)alkyl.

In one embodiment $R^{10}$ is —H, —OH, methyl, ethyl, propyl, butyl, t-butyl, acetyl, —COOMe, —$NH_2$, —NH(Me) or —$N(Me)_2$. In another embodiment $R^{10}$ is —H or methyl.

According one embodiment $A^2$ is —CH, $A^3$ is —$CR^7$ and —$CR^7$— is —C(OH), —C(CN), —C(F), —C(Cl), —C(OMe), —C(Me), —C(Et), —C($CHF_2$) or —C($CF_3$).

In one embodiment $A^2$ is —CH, $A^4$ is —$CR^8$ and —$CR^8$ is —C(OH), —C(CN), —C(F), —C(Cl), —C(OMe), —C(Me), —C(Et), —C($CF_3$), —C(aminoalkylene), —C(SMe) or —C[C(O)Me].

In one embodiment $A^2$ is —$CR^6$ and —C($R^6$) is —C(OH), —C(CN), —C(F), —C(Cl), —C(OMe), —C(Me), —C(Et), —C($CF_3$), or —C($NH_2$).

In one embodiment $W^1$ is O, Y is —NH and $A^1$ is —NH.

The inventive compounds according to Formula IA or Formula IB may be isotopically-labeled by having one or more atoms replaced by an atom having a different atomic mass or mass number. Examples of isotopes that can be incorporated into compounds according to Formula IA or Formula IB include isotopes of hydrogen, carbon, nitrogen, oxygen, phosphorous, fluorine, chlorine, or iodine. Illustrative of such isotopes are $^2$H, $^3$H, $^{11}$H, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds can be used to measure the biodistribution, tissue concentration and the kinetics of transport and excretion from biological tissues including a subject to which such a labeled compound is administered. Labeled compounds are also used to determine therapeutic effectiveness, the site or mode of action, and the binding affinity of a candidate therapeutic to a pharmacologically important target. Certain radioactively-labeled compounds according to Formula IA or Formula IB, therefore, are useful in drug and/or tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to Formula IA or Formula IB can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formula IA or Formula IB. Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabeled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

The invention also provides pharmaceutically acceptable salt forms of Formula IA and Formula IB compounds. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

Compounds of the invention or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule.

For example, in Formula IA when $W^1$ is oxo and —$NR^3$ is —NH the present invention provides tautomers as illustrated below:

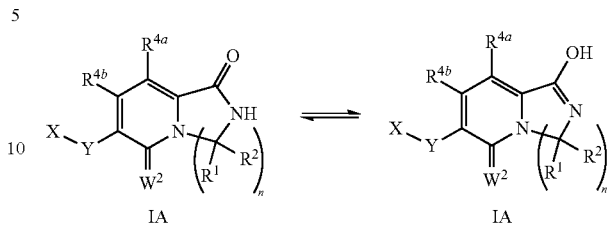

For Formula IB compounds, when $W^1$ is oxo and $A^1$ is —NH, the present invention provides the tautomer illustrated below:

The inventive compounds are synthesized using conventional synthetic methods, and more specifically using the general methods noted below. Specific synthetic protocols for compounds in accordance with the present invention are described in the Examples.

Pharmaceutical Formulations

In one embodiment, a compounds according Formula IA or Formula IB are formulated as pharmaceutically acceptable compositions that contain a Formula IA or Formula IB compound in an amount effective to treat a particular disease or condition of interest upon administration of the pharmaceutical composition to a mammal. Pharmaceutical compositions in accordance with the present invention can comprise a Formula IA or Formula IB compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula IA or Formula IB is administered to a mammal in an amount sufficient to inhibit Mnk activity upon administration, and preferably with acceptable toxicity to the same. Mnk activity of Formula IA or Formula IB compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a Mnk related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of Mnk and/or can be useful in analyzing Mnk signaling activity in model systems and/or for preventing, treating, or ameliorating a symptom associated with a disease, disorder, or pathological condition involving Mnk, preferably one afflicting humans. A compound which inhibits the activity of Mnk will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mnk, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a Mnk dependent condition in a mammal in need thereof, the method comprising administering an effective amount of a pharmaceutical composition as described above (i.e., a pharmaceutical composition comprising any one or more compounds of Formula IA or Formula IB) to a mammal.

As described above deregulation of protein synthesis is a common event in human cancers. A key regulator of translational control is eIF4E whose activity is a key determinant of tumorigenicity. Because activation of eIF4E involves phosphorylation of a key serine (Ser209) specifically by MAP kinase interacting kinases (Mnk), inhibitors of Mnk are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; acute and chronic leukemia, both myeloid and lymphoid/lymphoblastic, including hairy cell leukemia; histiocytosis malignant; Hodgkin's disease; immunoproliferative small; Hodgkin's lymphoma; B-cell and T-cell non-Hodgkin's lymphoma, including diffuse large B-cell and Burkitt's lymphoma; plasmacytoma; reticuloendotheliosis; melanoma; multiple myeloma; chondroblastoma; chondroma; chondrosarcoma; fibroma; fibrosarcoma; myelofibrosis; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment the present disclosure provides methods for treating colon cancer, colorectal cancer, gastric cancer, thyroid cancer, lung cancer, leukemia, pancreatic cancer, melanoma, multiple melanoma, brain cancer, primary and secondary CNS cancer, including malignant glioma and glioblastoma, renal cancer, prostate cancer, including castration-resistant prostate cancer, ovarian cancer, or breast cancer, including triple negative, HER2 positive, and hormone receptor positive breast cancers. According to such a method, a therapeutically effective amount of at least one compound according to Formula I or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula I or a stereoisomer, tautomer or pharmaceutically acceptable salt thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments the inventive Mnk inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments a Mnk inhibitor in accordance with the present invention is used simultaneously, in the same formulation or in separate formulations, or sequentially with an additional agent(s) as part of a combination therapy regimen.

Mnk inhibitors according to Formula IA or Formula IB including their corresponding salts and pharmaceutically acceptable compositions are effective as therapeutic agents for treating or preventing cytokine mediated disorders, such as inflammation in a patient, preferably in a human. In one embodiment, a compound or composition in accordance with the invention is particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The inventive compounds their corresponding salts and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a Formula IA or Formula IB compound, its pharmaceutically acceptable salt form, or a pharmaceutically acceptable composition of a Formula IA or Formula IB compound or its salt.

The invention also supports the use of the inventive compounds or a pharmaceutically acceptable formulation of the inventive compound as an inhibitor of Mnk activity. Such inhibition is achieved by contacting a cell expressing Mnk with a compound or a pharmaceutically acceptable formulation, to lower or inhibit Mnk activity, to provide therapeutic efficacy for a Mnk dependent condition in a mammal in need thereof.

Therapeutically effective dosages of a compound according to Formula IA or Formula IB or a composition of a Formula IA or Formula IB compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

General Synthetic Methods for Formula IA Compounds
Method 1:

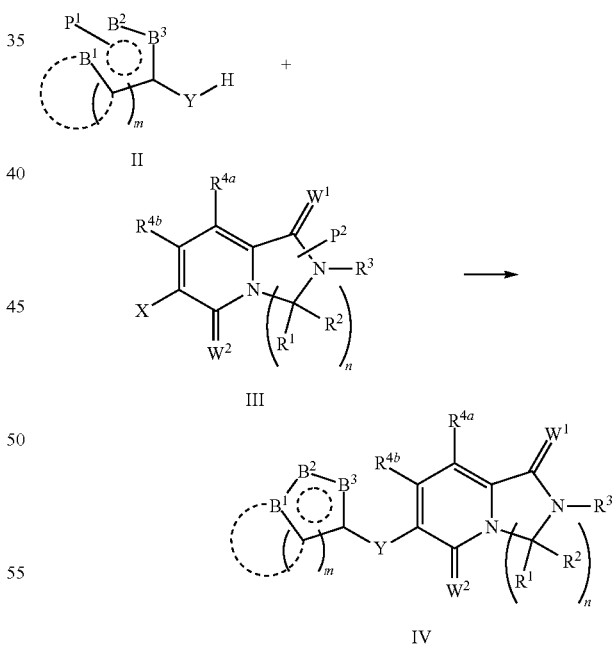

The formation of IV (Y is —NR$^8$) is accomplished by contacting compound II (P$^1$ is an optional protecting group) and compound III (X is a leaving group, such as halogen, —OTf, —OTs or —OMs, and P$^2$ is an optional protecting group) under the Buchwald-Hartwig conditions (such as palladium catalyst, ligand, base, solvent and heat), followed by de-protection and/or further functional group manipulation if necessary.

Alternatively, formation of IV (Y is —NR$^8$, —O—) is accomplished by contacting compound II (P$^1$ is an optional protecting group) and compound III (X is a leaving group, such as halogen, —OTf, —OTs or —OMs, and P$^2$ is an optional protecting group) under the copper-mediated Ullmann type conditions (such as copper(I) iodide, base, solvent and heat), followed by de-protection and/or further functional group manipulation if necessary.

Alternatively, formation of IV (Y is —NR$^8$, —O—, —S—) is accomplished by contacting compound II (P$^1$ is an optional protecting group) and compound III (X is a leaving group, such as halogen, —OTf, —OTs or —OMs, and P$^2$ is an optional protecting group) under the nucleophilic aromatic substitution conditions (such as base or acid, solvent and heat), followed by de-protection and/or further functional group manipulation if necessary.

It is understood that if protecting groups are used during the synthesis of intermediates, or if a Formula IA compound contains one or more protecting groups, then such protecting groups are removed by methods known in the chemical art. Other transformations, such as the displacement of a halogen, for example, the conversion of R$^{4a}$ or R$^{4b}$=Cl to R$^{4a}$ or R$^{4b}$=OMe, SMe, CH=CH$_2$ or Me, the conversion of W$^1$ or W$^2$ or both groups from O to S, the formation of an oxime by converting W$^1$ or W$^2$ or both groups from an oxo (O) group to —NO(R$^9$), the conversion of Y from S to S(O) or S(O)$_2$, the conversion of W$^1$ from O to CR$^{9a}$R$^{9b}$, and the conversion of an intermediate or a Formula IA compound to a pharmaceutically acceptable salt are carried out using conventional methods known in the chemical art.

Method 2:

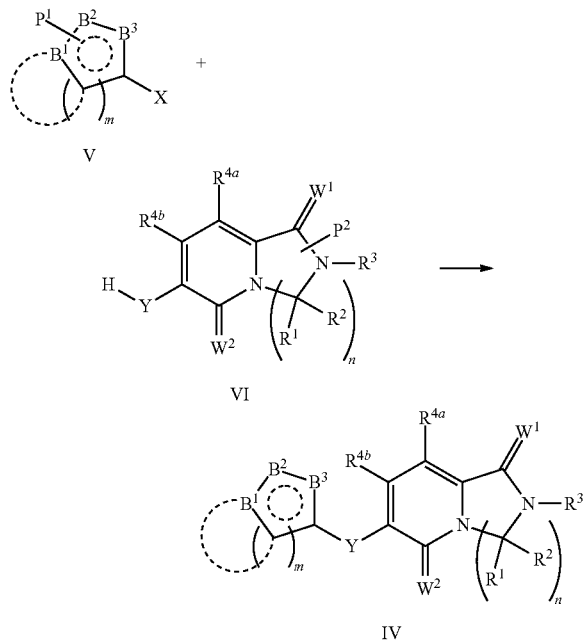

Alternatively, formation of IV (Y is —NR$^8$, —O—) is accomplished by contacting compound V (X is a leaving group, such as halogen, —OTf, —OTs or —OMs, and P$^1$ is an optional protecting group) with compound VI (P$^2$ is an optional protecting group) under the copper-mediated Ullmann type conditions (such as copper(I) iodide, base, solvent and heat), followed by de-protection and/or further functional group manipulation if necessary.

Alternatively, formation of IV (Y is —NR$^8$, —O—, —S—) is accomplished by contacting compound V (X is a leaving group, such as halogen, —OTf, —OTs or —OMs, and P$^1$ is an optional protecting group) with compound VI (P$^2$ is an optional protecting group) under the nucleophilic aromatic substitution conditions (such as base or acid, solvent and heat), followed by de-protection and/or further functional group manipulation if necessary.

Method 3:

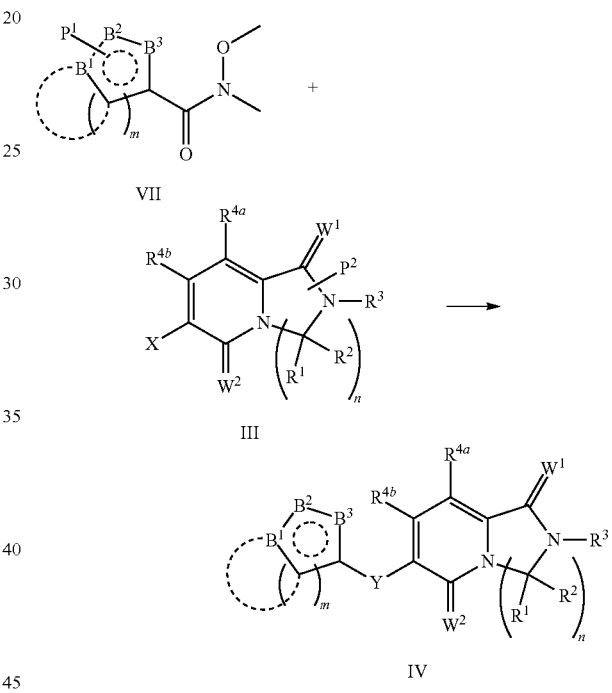

The formation of IV (Y is —C(O)—) is accomplished by contacting compound VII (P$^1$ is an optional protecting group) with compound III (X is a leaving group, such as halogen, —OTf, —OTs or —OMs, and P$^2$ is an optional protecting group) in the presence of a base such as n-butyllithium, followed by de-protection and/or further functional group manipulation if necessary.

The formation of IV (Y is —CH(OH)) is accomplished by reducing IV (Y is —C(O)—) in the presence of a reducing reagent such as sodium borohydride, followed by de-protection and/or further functional group manipulation if necessary.

The formation of IV (Y is —CH$_2$—) is accomplished by exposing IV (Y is —C(O)—) to the conditions of Clemmensen reduction (such as zinc mercury amalgam, acid, solvent and heat) or Wolff-Kishner reduction (such as hydrazine, base, solvent, heat), followed by de-protection and/or further functional group manipulation if necessary.

The formation of IV (Y is —CH[(C$_1$-C$_4$)alkyl]) is accomplished by exposing IV (Y is —C(O)—) to the conditions of Wittig olefination (such as Ph$_3$P[(C$_1$-C$_4$)alkyl]Br, base, sol- The formation of IV (Y is —NR$^8$) is accomplished by contacting compound V (X is a leaving group, such as halogen, —OTf, —OTs or —OMs, and P$^1$ is an optional protecting group) with compound VI (P$^2$ is an optional protecting group) under the Buchwald-Hartwig conditions (such as palladium catalyst, ligand, base, solvent and heat), followed by de-protection and/or further functional group manipulation if necessary.

vent and heat), followed by hydrogenation (such as hydrogen, 10% palladium on carbon, solvent), then followed by de-protection and/or further functional group manipulation if necessary.

Method 4:

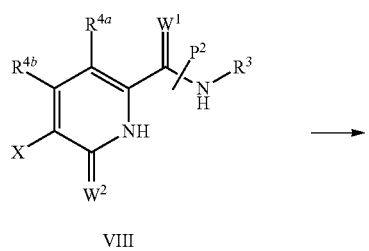

VIII

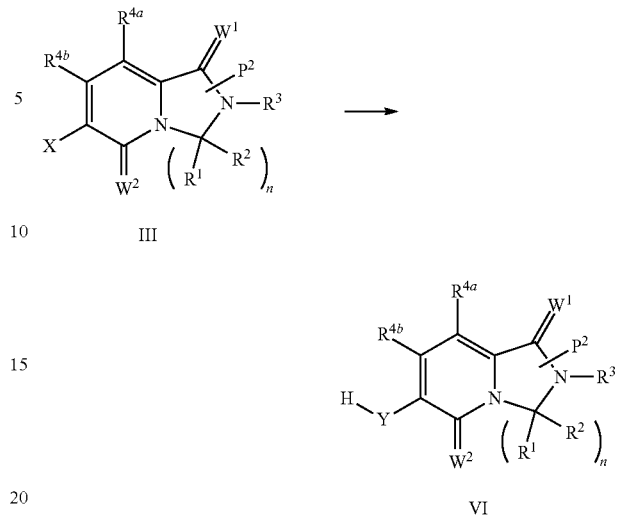

III

VI

Method 5:

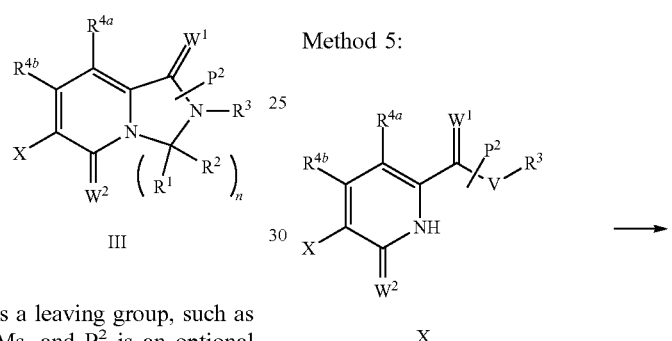

X

III

The formation of III (n=1, X is a leaving group, such as halogen, —OTf, —OTs or —OMs, and P² is an optional protecting group) is accomplished by exposing intermediate VIII to an aldehyde or ketone IXa, or an aldehyde or ketone equivalent IXb-d under acidic conditions where $R^1$, $R^2$ are as defined in the specification and R'=H, $CH_3$, $CH_2CH_3$, or alkyl. More specifically, exposing VIII where X is Cl or Br to an aldehyde or ketone IXa in 1,4-dioxane and concentrated sulfuric acid with heating yields intermediate III (n=1).

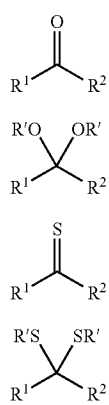

IXa

IXb

IXc

IXd

Alternatively, the leaving group X of intermediate III may be displaced with an appropriate N, O, or S nucleophile under conditions similar to those described above for synthesis of IV so as to afford intermediate VI where Y is —$NR^8$, —O—, or —S—.

The formation of III (n=2 or 3, X is a leaving group, such as halogen, —OTf, —OTs or —OMs, V is O or N, and $P^2$ is an optional protecting group) are accomplished by contacting intermediate X to a 1,2-difunctionalized ethyl intermediate XIa, or a 1,3-difunctionalized propyl intermediate XIb under conditions suitable for the synthesis of compounds III known in the chemical art. Variables $Z^1$ and $Z^2$ in XIa and XIb can be a halogen or other leaving groups such as —OTf, —OTs or —OMs, or OH, $NHR^1$ or NHP, where P is an appropriate protecting group.

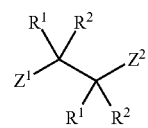

XIa

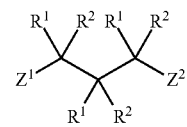

XIb

General Synthetic Methods for Formula IB Compounds
Method 1:

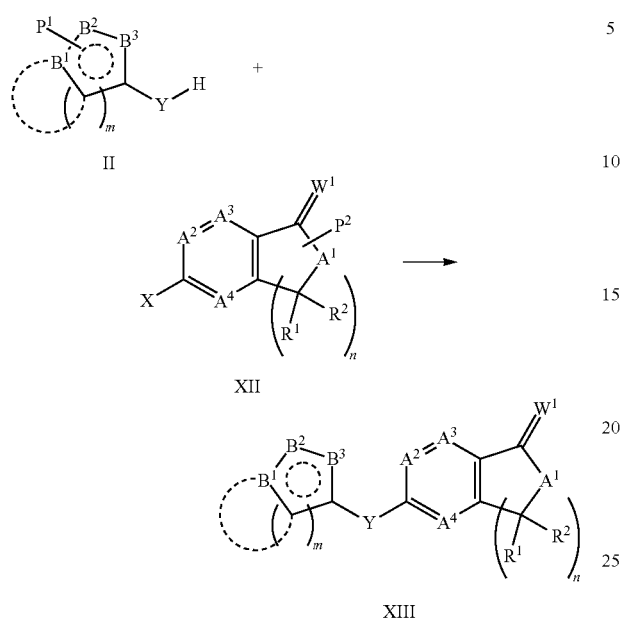

II

XII

XIII

Method 2:

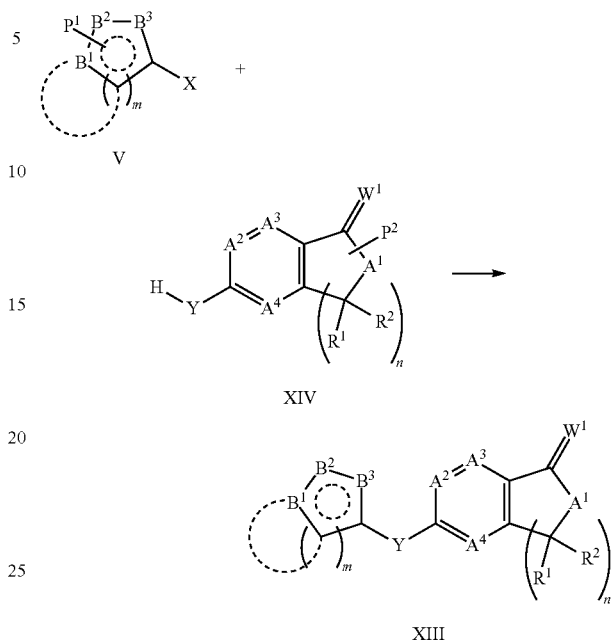

V

XIV

XIII

The formation of compound XIII (Y is —NR$^8$) according to Formula IB is accomplished by contacting compound II (P$^1$ is an optional protecting group) with compound XII (X is a leaving group, such as halogen, —OTf, —OTs or —OMs, and P$^2$ is an optional protecting group) under the Buchwald-Hartwig conditions (such as palladium catalyst, ligand, base, solvent and heat) followed by de-protection and/or further functional group manipulation if necessary.

Alternatively, the formation of compound XIII (Y is —NR$^8$, —O—) is accomplished by contacting compound II (P$^1$ is an optional protecting group) with compound XII (X is a leaving group, such as halogen, —OTf, —OTs or —OMs, and P$^2$ is an optional protecting group) under the copper-mediated Ullmann type conditions (such as copper(I) iodide, base, solvent and heat) followed by de-protection and/or further functional group manipulation if necessary.

Alternatively, the formation of compound XIII (Y is —NR$^8$, —O—, —S—) is accomplished by contacting compound II (P$^1$ is an optional protecting group) with compound XII (X is a leaving group, such as halogen, —OTf, —OTs or —OMs, and P$^2$ is an optional protecting group) under the nucleophilic aromatic substitution conditions (such as base or acid, solvent and heat) followed by de-protection and/or further functional group manipulation if necessary.

It is understood that if protecting groups are used during the synthesis of intermediates, or if a Formula IB compound contains one or more protecting groups, then such protecting groups are removed by methods known in the chemical art. Other transformations, such as the displacement of a halogen, for example, the conversion of R$^{4a}$ or R$^{4b}$=Cl to R$^{4a}$ or R$^{4b}$=OMe, SMe, CH=CH$_2$ or Me, the conversion of W$^1$ or W$^2$ or both groups from O to S, the formation of an oxime by converting W$^1$ or W$^2$ or both groups from an oxo (O) group to =NO(R$^9$), the conversion of Y from S to S(O) or S(O)$_2$, the conversion of W$^1$ from O to CR$^{9a}$R$^{9b}$, and the conversion of an intermediate or a Formula IB compound to a pharmaceutically acceptable salt are carried out using conventional methods known in the chemical art.

The formation of compound XIII (Y is —NR$^8$) is accomplished by contacting compound V (X is a leaving group, such as halogen, —OTf, —OTs or —OMs, and P$^1$ is an optional protecting group) with compound XIV (P$^2$ is an optional protecting group) under the Buchwald-Hartwig conditions (such as palladium catalyst, ligand, base, solvent and heat) followed by de-protection and/or further functional group manipulation if necessary.

Alternatively, the formation of compound XIII (Y is —NR$^8$, —O—) is accomplished by contacting compound V (X is a leaving group, such as halogen, —OTf, —OTs or —OMs, and P$^1$ is an optional protecting group) with compound XIV (P$^2$ is an optional protecting group) under the copper-mediated Ullmann type conditions (such as copper(I) iodide, base, solvent and heat) followed by de-protection and/or further functional group manipulation if necessary.

Alternatively, the formation of compound XIII (Y is —NR$^8$, —O—, —S—) is accomplished by contacting compound V (X is a leaving group, such as halogen, —OTf, —OTs or —OMs, and P$^1$ is an optional protecting group) with compound XIV (P$^2$ is an optional protecting group) under the nucleophilic aromatic substitution conditions (such as base or acid, solvent and heat) followed by de-protection and/or further functional group manipulation if necessary.

Method 3:

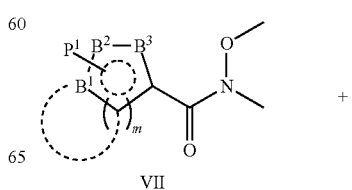

VII

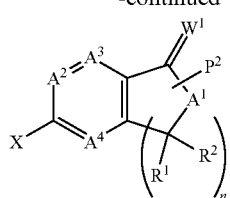

XII

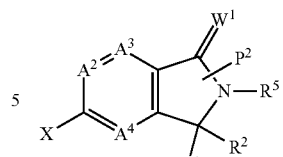

XVI

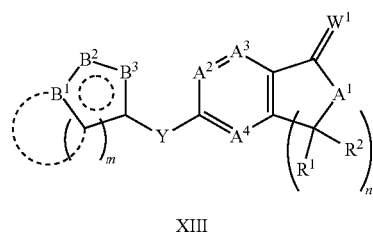

XIII

The formation of compound XIII (Y is —C(O)—) is accomplished by contacting compound VII (P¹ is an optional protecting group) with compound XII (X is a leaving group, such as halogen, —OTf, —OTs or —OMs, and P² is an optional protecting group) in the presence of a base such as n-butyllithium, followed by de-protection and/or further functional group manipulation if necessary.

The formation of compound XIII where Y is —CH(OH)— is accomplished by reducing XIII where Y is —C(O)—, with an appropriate reducing reagent, for example, sodium borohydride, followed by de-protection and/or further functional group manipulation if necessary.

The formation of compound XIII where Y is —CH$_2$— is accomplished by exposing XIII where Y is —C(O)— to the conditions of Clemmensen reduction (such as zinc mercury amalgam, acid and heat) or Wolff-Kishner reduction (such as hydrazine, base and heat) followed by de-protection and/or further functional group manipulation if necessary.

Method 4:

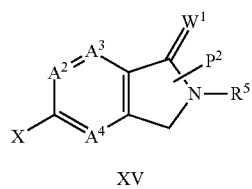

XV

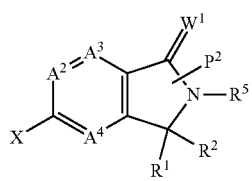

XVI

The formation of intermediate XVI (X is a leaving group, such as halogen, —OTf, —OTs or —OMs, and P² is an optional protecting group) is accomplished by exposing compound XV to a suitable alkyl halide under basic conditions (such as sodium hydride and solvent).

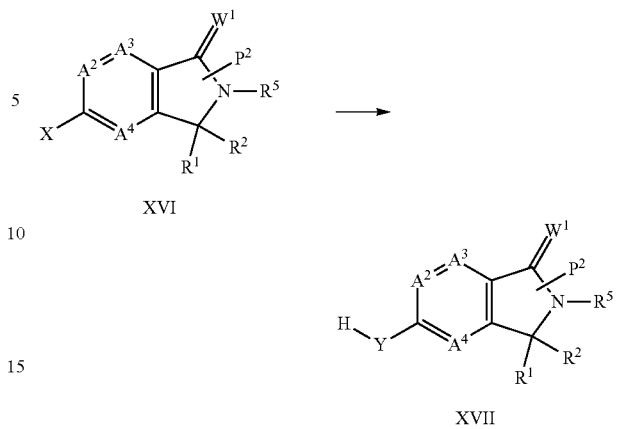

XVII

Alternatively, the leaving group X of intermediate XVI may be displaced with an appropriate N, O, or S nucleophile under conditions similar to those described above for synthesis of XIII so as to afford intermediate XVII where Y is —NR$^8$, —O—, or —S—.

EXAMPLES

The following examples are provided for purpose of illustration and not limitation.

Example 1

Synthesis of 6'-((1,3,4-thiadiazol-2-yl)amino)-8'-chloro-2'H spiro[cyclohexane-1,3'-imidazo[1,5-a]pyridine]-1',5'-dione (Cpd. No. 1F)

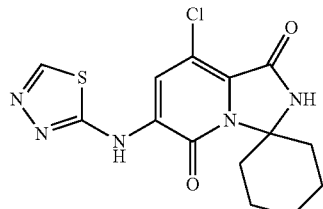

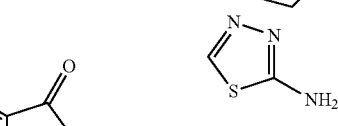

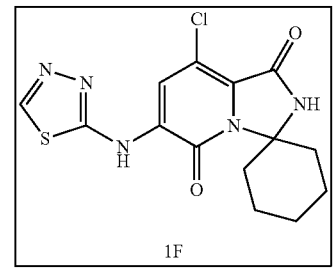

1F

Synthesis of 6'-((1,3,4-thiadiazol-2-yl)amino)-8'-chloro-2'H-spiro[cyclohexane-1,3'-imidazo[1,5-a]pyridine]-1',5'-dione (Cpd. No. 1F)

A vial containing 1,4-dioxane (10 mL) was charged with 6'-bromo-8'-chloro-2'H-spiro[cyclohexane-1,3'-imidazo[1,5-a]pyridine]-1',5'-dione (1, 0.25 g, 0.754 mmol), 1,3,4-thiadiazol-2-amine (2, 0.076 g, 0.754 mmol) and cesium carbonate (0.74 g, 2.26 mmol) and the mixture was purged with argon for 5 min. XantPhos (0.021 g, 0.037 mmol), XPhos (0.018 g, 0.037 mmol), tris(dibenzylideneacetone)dipalladium(0) (0.035 g, 0.037 mmol) and palladium (II) acetate (0.008 g, 0.037 mmol) were then added and the mixture was purged for another 5 min. The vial was sealed and the reaction mixture was heated at 110° C. for 2 h. After completion, the reaction mass was diluted with 5% methanol in dichloromethane (150 mL) and passed through a bed of alumina. The crude was concentrated and purified by column chromatography eluting with 2-5% methanol in dichloromethane. The desired fractions were concentrated to afford 6'-((1,3,4-thiadiazol-2-yl)amino)-8'-chloro-2'H-spiro[cyclohexane-1,3'-imidazo[1,5-a]pyridine]-1',5'-dione (Cpd. No. 1F) as an off-white solid. Yield: 0.110 g, 42%; MS (ESI) m/z 352.41 [M+1]$^+$; $^1$H NMR (400 MHz, DMSO-d$_6$) δ 10.76 (s, 1H), 10.30 (s, 1H), 9.04 (s, 1H), 8.62 (s, 1H), 2.98-2.90 (m, 2H), 1.82-1.50 (m, 7H), 1.30-1.15 (m, 1H).

Synthesis of 6'-((1,2,4-thiadiazol-5-yl)amino)-8'-chloro-2'H-spiro[cyclohexane-1,3'-imidazo[1,5-a]pyridine]-1',5'-dione (Cpd. No. 2F)

A vial containing 1,4-dioxane (5 mL) was charged with 6'-bromo-8'-chloro-2'H-spiro[cyclohexane-1,3'-imidazo[1,5-a]pyridine]-1',5'-dione (1, 0.20 g, 0.60 mmol), 1,2,4-thiadiazol-5-amine (2, 0.067 g, 0.60 mmol) and cesium carbonate (0.59 g, 1.80 mmol). The reaction mixture was purged with argon for 5 min. XantPhos (0.017 g, 0.030 mmol), XPhos (0.014 g, 0.030 mmol), tris(dibenzylideneacetone)dipalladium(0) (0.027 g, 0.030 mmol) and palladium(II) acetate (0.007 g, 0.030 mmol) were added and the mixture was purged for another 5 min. The vial was sealed and the reaction mixture was heated at 110° C. for 2 h. After completion, the reaction mass was diluted with 5% methanol in dichloromethane (150 mL) and passed through a bed of alumina. The crude was concentrated and purified by column chromatography using 2-5% methanol in dichloromethane. The desired fractions were concentrated to afford 6'-((1,2,4-thiadiazol-5-yl)amino)-8'-chloro-2'H-spiro[cyclohexane-1,3'-imidazo[1,5-a]pyridine]-1',5'-dione (Cpd. No. 2F) as an off-white solid. Yield: 0.085 g, 40%; MS (ESI) m/z 352.39[M+1]$^+$; $^1$H NMR (400 MHz, DMSO-d$_6$) δ 11.24 (s, 1H), 10.33 (s, 1H), 8.62 (s, 1H), 8.36 (s, 1H), 2.96-2.85 (m, 2H), 1.80-1.46 (m, 7H), 1.27-1.16 (m, 1H).

Example 2

Synthesis of 6'-((1,2,4-thiadiazol-5-yl)amino)-8'-chloro-2'H-spiro[cyclohexane-1,3'-imidazo[1,5-a]pyridine]-1',5'-dione (Cpd. No. 2F)

Example 3

Synthesis of 6'-((1,2,3-thiadiazol-5-yl)amino)-8'-chloro-2'H-spiro[cyclohexane-1,3'-imidazo[1,5-a]pyridine]-1',5'-dione (Cpd. No. 3)

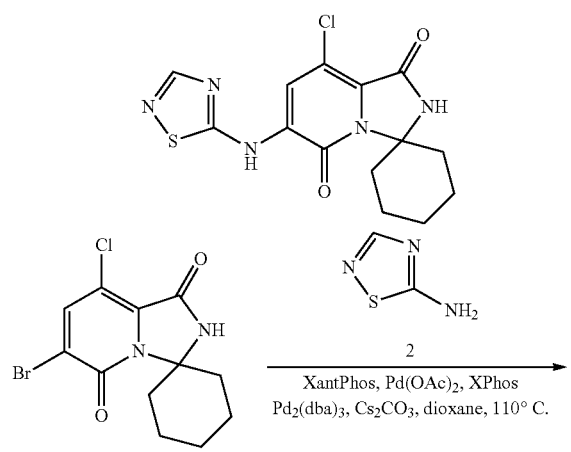

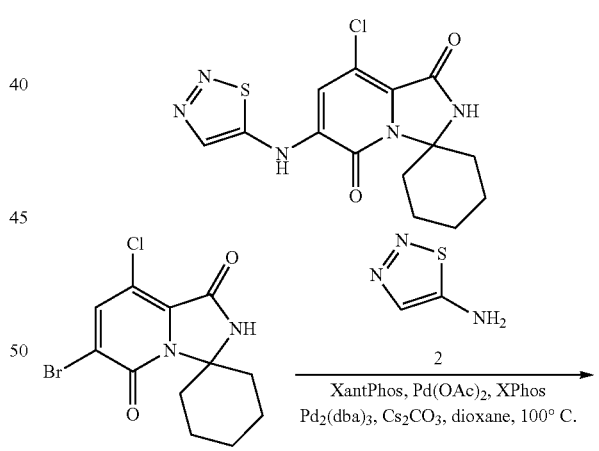

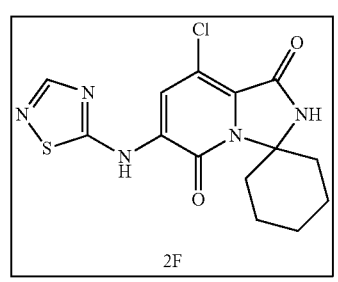

Synthesis of 6'-((1,2,3-thiadiazol-5-yl)amino)-8'-chloro-2'H-spiro[cyclohexane-1,3'-imidazo[1,5-a]pyridine]-1',5'-dione (Cpd. No. 3)

To a solution of 6-bromo-8-chloro-spiro[2H-imidazo[1,5-a]pyridine-3,1'-cyclohexane]-1,5-dione (1, 0.3 g, 0.906 mmol) and 1,2,3-thiadiazol-5-amine (2, 0.082 g, 0.815 mmol) in dioxane (15 mL), cesium carbonate (0.88 g, 2.71 mmol) was added and the mixture was purged with argon for 10 min. XantPhos (0.026 g, 0.045 mmol), palladium(II) acetate (0.010 g, 0.045 mmol), XPhos (0.021 g, 0.045 mmol) and tris(dibenzylideneacetone)dipalladium(0) (0.041 g, 0.045 mmol) were added and mixture was purged for another 5 min. The vial was sealed and the reaction mixture was heated at 100° C. for 4 h. After completion, the reaction mixture was filtered over a bed of celite. The bed was washed with 5% methanol in dichloromethane and the filtrate was concentrated. The crude was triturated with methanol followed by ether, pentane and dried under vacuum to afford 6'-((1,2,3-thiadiazol-5-yl)amino)-8'-chloro-2'H-spiro[cyclohexane-1,3'-imidazo[1,5-a]pyridine]-1',5'-dione (Cpd. No. 3) as a yellow solid. Yield: 0.21 g, 66%; MS (ESI) m/z 352.37[M+1]$^+$; $^1$H NMR (400 MHz, DMSO-d$_6$) δ 10.32 (s, 1H), 7.42 (s, 1H), 6.41 (s, 1H), 2.94-2.87 (m, 2H), 1.75-1.45 (m, 7H), 1.26-1.18 (m, 1H).

Example 4

Synthesis of 6'-((1H-1,2,4-triazol-5-yl)amino)-8'-chloro-2'H-spiro[cyclohexane-1,3'-imidazo[1,5-a]pyridine]-1',5'-dione (Cpd. No. 4F)

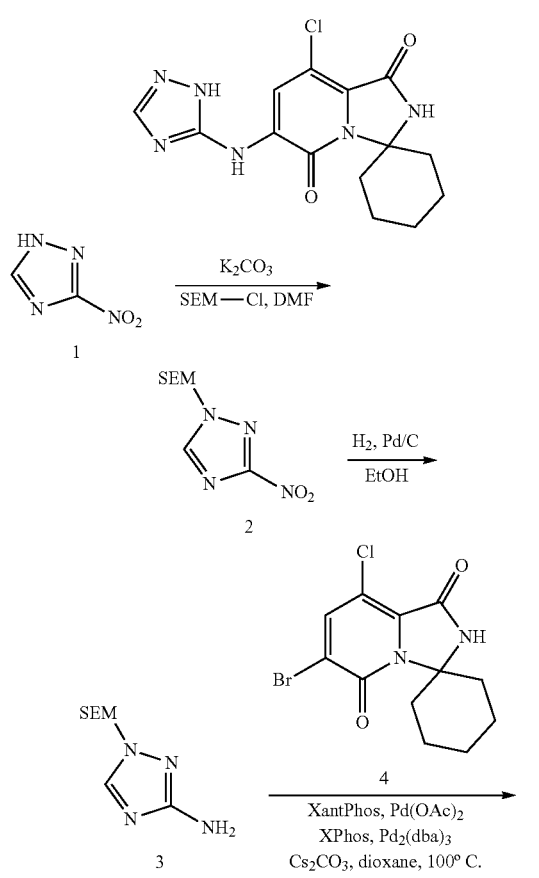

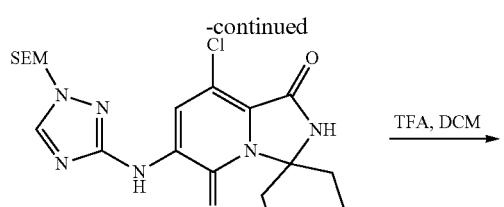

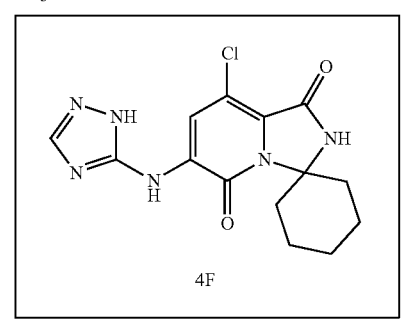

Synthesis of 3-nitro-1-((2-(trimethylsilyl)ethoxy)methyl)-1H-1,2,4-triazole (2)

To a solution of 3-nitro-1H-1,2,4-triazole (1, 1.0 g, 8.76 mmol) in dimethylformamide (10 mL), potassium carbonate (3.62 g, 26.2 mmol) and 2-(trimethylsilyl)ethoxymethyl chloride (1.6 g, 9.64 mmol) were added. The reaction mixture was stirred at room temperature for 3 h. After completion, ice water (25 mL) was added and the reaction was extracted with ethyl acetate (100 mL). The organic layer was washed with saturated ammonium chloride solution (25 mL), brine (25 mL), dried over anhydrous sodium sulfate, filtered and concentrated to afford 3-nitro-1-((2-(trimethylsilyl)ethoxy)methyl)-1H-1,2,4-triazole (2) as a white solid. Yield: 0.91 g, 42%; MS (ESI) m/z 303.16 [M+AcO$^-$]$^-$.

Synthesis of 1-((2-(trimethylsilyl)ethoxy)methyl)-1H-1,2,4-triazol-3-amine (3)

To a solution of 3-nitro-1-((2-(trimethylsilyl)ethoxy)methyl)-1H-1,2,4-triazole (2, 0.9 g, 3.68 mmol) in ethanol (10 mL), 10% palladium on carbon (0.180 g) was added. The reaction was purged with hydrogen and allowed to stir at room temperature for 3 h. After completion, the reaction mass was passed through a bed of celite and the filtrate was evaporated under reduced pressure to afford 1-((2-(trimethylsilyl)ethoxy)methyl)-1H-1,2,4-triazol-3-amine (3) as a light brown solid. Yield: 0.6 g, 76%; MS (ESI) m/z 215.14 [M+1]$^+$.

Synthesis of 8'-chloro-6'-((1-((2-(trimethylsilyl)ethoxy)methyl)-1H-1,2,4-triazol-3-yl)amino)-2'H-spiro[cyclohexane-1,3'-imidazo[1,5-a]pyridine]-1',5'-dione (5)

A vial was charged with 6'-bromo-8'-chloro-2'H-spiro[cyclohexane-1,3'-imidazo[1,5-c]pyridine]-1',5'-dione (4, 0.5 g, 1.13 mmol), 1-((2-(trimethylsilyl)ethoxy)methyl)-1H-1,2,4-triazol-3-amine (3, 0.290 g, 1.36 mmol) and 1,4-dioxane (10 mL) followed by the addition of cesium carbonate (1.1 g, 3.39 mmol). The mixture was purged with argon for 5 minutes and XantPhos (0.037 g, 0.065 mmol), palladium(II) acetate (0.014 g, 0.065 mmol), XPhos (0.030 g, 0.075 mmol) and tris(dibenzylideneacetone)dipalladium (0) (0.060 g, 0.065 mmol) were added and the mixture was purged for another 5 minutes. The vial was sealed and the reaction mixture was heated at 100° C. for 3 h. After completion, the reaction mixture was concentrated to obtain a solid which was washed with water followed by a minimum amount of methanol, ether and pentane. The solid was dried under vacuum to afford 8'-chloro-6'-((1-((2-(trimethylsilyl)ethoxy)methyl)-1H-1,2,4-triazol-3-yl)amino)-2'H-spiro[cyclohexane-1,3'-imidazo[1,5-a]pyridine]-1',5'-dione (5) as a light yellow solid. Yield: 0.45 g, 85%; MS (ESI) m/z 465.44[M+1]⁺.

Synthesis of 6'-((1H-1,2,4-triazol-5-yl)amino)-8'-chloro-2'H-spiro[cyclohexane-1,3'-imidazo[1,5-a]pyridine]-1',5'-dione (Cpd. No. 4F)

To a solution of 8'-chloro-6'-((1-((2-(trimethylsilyl)ethoxy)methyl)-1H-1,2,4-triazol-3-yl)amino)-2'H-spiro[cyclohexane-1,3'-imidazo[1,5-a]pyridine]-1',5'-dione (5, 0.35 g, 0.75 mmol) in dichloromethane (5 mL), trifluoroacetic acid (5 mL) was added at 0° C. and the reaction mixture was stirred at room temperature for 18 h. After the completion of the reaction, water (20 mL) was added and the mixture was extracted with 5% methanol in dichloromethane (100 mL). The organic layer was washed with water and brine, dried over anhydrous sodium sulfate, filtered and concentrated. The crude was washed with ether, pentane and dried under vacuum to afford 6'-((1H-1,2,4-triazol-5-yl)amino)-8'-chloro-2'H-spiro[cyclohexane-1,3'-imidazo[1,5-a]pyridine]-1',5'-dione (Cpd. No. 4F) as an off-white solid. Yield: 0.12 g, 46%; MS (ESI) m/z 335.34[M+1]⁺; ¹H NMR (400 MHz, DMSO-d₆) δ 13.72 (brs, 1H), 10.20 (s, 1H), 8.50 (brs, 2H), 8.07 (s, 1H), 2.96-2.90 (m, 2H), 1.81-1.73 (m, 2H), 1.68-1.61 (m, 3H), 1.53-1.50 (m, 2H), 1.30-1.18 (m, 1H).

Example 5

Synthesis of 8'-chloro-6'-(thiazol-5-ylamino)-2'H-spiro[cyclohexane-1,3'-imidazo[1,5-a]pyridine]-1',5'-dione (Cpd. No. 5)

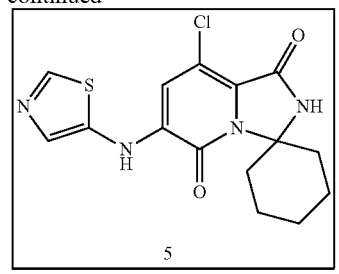

Synthesis of 8'-chloro-6'-(thiazol-5-ylamino)-2'H-spiro[cyclohexane-1,3'-imidazo[1,5-a]pyridine]-1',5'-dione (Cpd. No. 5)

To a solution of 6-bromo-8-chloro-spiro[2H-imidazo[1,5-a]pyridine-3,1'-cyclohexane]-1,5-dione (1, 0.3 g, 0.91 mmol) and thiazol-5-amine (2, 0.11 g, 1.09 mmol) in 1,4-dioxane (15 mL), cesium carbonate (0.884 g, 2.71 mmol) was added and the mixture was purged with argon for 15 min. XantPhos (0.026 g, 0.045 mmol), palladium(II) acetate (0.020 g, 0.090 mmol), and XPhos (0.021 g, 0.045 mmol) were added and the mixture was purged for another 5 min. The vial was sealed and the reaction mixture was heated at 100° C. for 14 h. After completion, the reaction mixture was filtered over a bed of celite and washed with 5% methanol in dichloromethane (100 mL). The filtrate was concentrated to get the crude which was washed with methanol followed by ether, pentane and dried under vacuum to afford 8'-chloro-6'-(thiazol-5-ylamino)-2'H-spiro[cyclohexane-1,3'-imidazo[1,5-a]pyridine]-1',5'-dione (Cpd. No. 5) as a yellow solid. Yield: 0.11 g, 35%; MS (ESI) m/z 351.31[M+1]⁺; ¹H NMR (400 MHz, DMSO-d₆) δ 10.14 (s, 1H), 9.05 (s, 1H), 8.86 (s, 1H), 7.77 (s, 1H), 6.65 (s, 1H), 2.98-2.90 (m, 2H), 1.80-1.47 (m, 7H), 1.28-1.17 (m, 1H).

Example 6

Synthesis of 6'-((1,2,5-thiadiazol-3-yl)amino)-8'-chloro-2'H-spiro[cyclohexane-1,3'-imidazo[1,5-a]pyridine]-1',5'-dione (Cpd. No. 6)

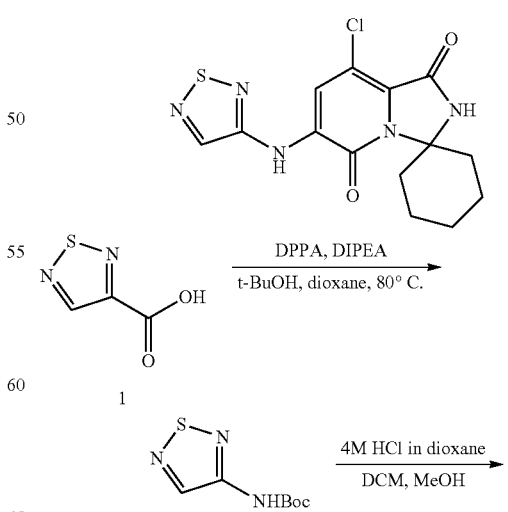

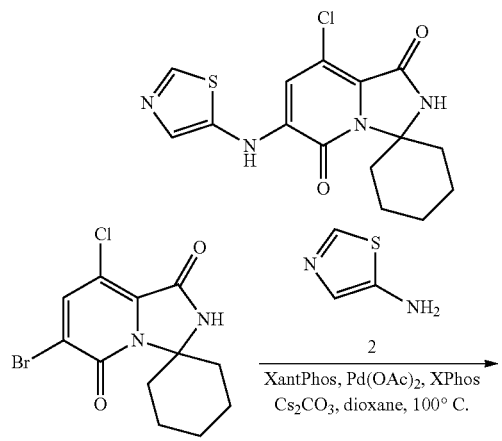

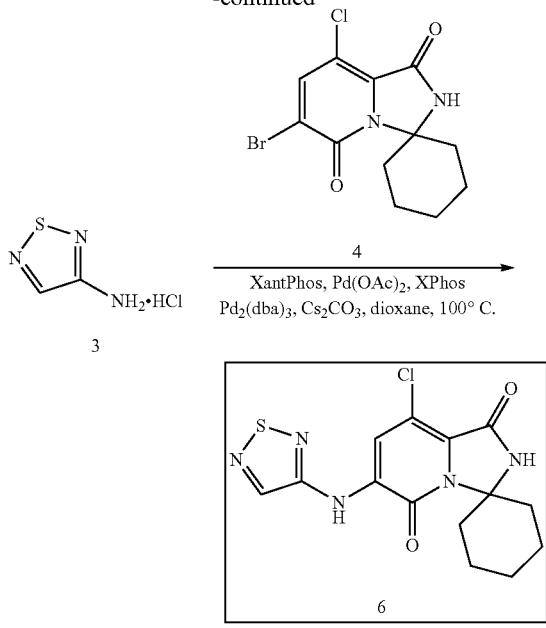

Synthesis of tert-butyl (1,2,5-thiadiazol-3-yl)carbamate (2)

A vial containing 1,4-dioxane (20 mL) was charged with 1,2,5-thiadiazole-3-carboxylic acid (1, 0.80 g, 1.15 mmol), N,N-diisopropylethylamine (1.19 g, 9.23 mmol), diphenylphosphoryl azide (2.37 g, 8.61 mmol) and tert-butanol (0.91 g, 12.30 mmol). The mixture was then heated to 85° C. for 16 h. After completion, the solvent was removed under reduced pressure and the crude was purified by column chromatography using 25-30% ethyl acetate in hexane. The desired fractions were concentrated to afford tert-butyl (1,2,5-thiadiazol-3-yl)carbamate (2) as a white solid. Yield: 0.50 g, crude.

Synthesis of 1, 2, 5-thiadiazol-3-amine hydrochloride (3)

A flask containing 1,4-dioxane (10 mL) was charged with tert-butyl (1,2,5-thiadiazol-3-yl)carbamate (2, 0.40 g, 1.99 mmol) and 4 M hydrogen chloride in 1,4-dioxane (5 mL) at room temperature. The reaction was stirred for 16 h. After completion, the solvent was removed under reduced pressure and the crude was triturated with dichloromethane and filtered. The solid was washed with ether and dried under high vacuum to afford 1, 2, 5-thiadiazol-3-amine hydrochloride (3) as a white solid. Yield: 0.13 g, crude.

Synthesis of 6'-((1,2,5-thiadiazol-3-yl)amino)-8'-chloro-2'H-spiro[cyclohexane-1,3'-imidazo[1,5-a]pyridine]-1',5'-dione (Cpd. No. 6)

A vial containing 1,4-dioxane (5 mL) was charged with 6'-bromo-8'-chloro-2'H-spiro[cyclohexane-1,3'-imidazo[1,5-a]pyridine]-1',5'-dione (4, 0.10 g, 0.30 mmol), 1,2,5-thiadiazol-3-amine hydrochloride (3, 0.042 g, 0.30 mmol) and cesium carbonate (0.30 g, 0.90 mmol). The mixture was purged with argon for 5 min. XantPhos (0.009 g, 0.015 mmol), XPhos (0.007 g, 0.015 mmol), tris(dibenzylideneacetone)dipalladium(0) (0.014 g, 0.015 mmol) and palladium (II) acetate (0.004 g, 0.015 mmol) were added and the mixture was purged for another 5 min. The vial was sealed and the reaction mixture was heated at 110° C. for 2 h. After completion, the reaction mass was diluted with 5% methanol in dichloromethane (50 mL) and passed through a bed of alumina. The crude was concentrated and purified via column chromatography using 2-5% methanol in dichloromethane. The desired fractions were concentrated to afford 6'-((1,2,4-thiadiazol-5-yl)amino)-8'-chloro-2'H-spiro[cyclohexane-1,3'-imidazo[1,5-a]pyridine]-1',5'-dione (Cpd. No. 6) as an off-white solid. Yield: 0.040 g, 33%; MS (ESI) m/z: 352.30[M+1]$^+$; $^1$H NMR (400 MHz, DMSO-d$_6$) δ 10.48 (brs, 1H), 10.28 (brs, 1H), 8.70 (s, 1H), 8.44 (s, 1H), 2.98-2.92 (m, 2H), 1.77-1.53 (m, 7H), 1.27-1.18 (m, 1H).

Example 7

Synthesis of 8'-chloro-6'-((2-methyl-2H-1,2,3-triazol-4-yl)amino)-2'H-spiro[cyclohexane-1,3'-imidazo[1,5-a]pyridine]-1',5'-dione (Cpd. No. 7)

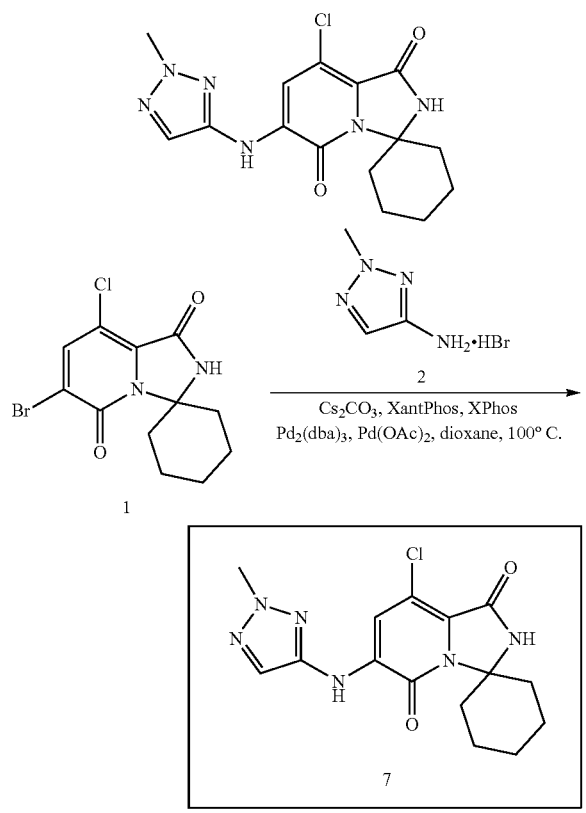

Synthesis of 8'-chloro-6'-((2-methyl-2H-1,2,3-triazol-4-yl)amino)-2'H-spiro[cyclohexane-1,3'-imidazo[1,5-a]pyridine]-1',5'-dione (Cpd. No. 7)

To a solution of 2-methyl-2H-1,2,3-triazol-4-amine hydrobromide (2, 0.1 g, 0.56 mmol) in 1,4-dioxane (5 mL), 6-bromo-8-chloro-spiro[2H-imidazo[1,5-a]pyridine-3,1'-cyclohexane]-1,5-dione (1, 0.18 g, 0.56 mmol) and cesium carbonate (0.73 g, 2.24 mmol) were added. The reaction mixture was purged with argon for 10 min and XantPhos (16 mg, 0.028 mmol), XPhos (13 mg, 0.028 mmol), tris(dibenzylideneacetone)dipalladium(0) (26 mg, 0.028 mmol) and palladium(II) acetate (6 mg, 0.028 mmol) were added. The reaction was purged with argon for another 2 min and stirred at 90° C. for 16 h. After completion, the reaction mass was diluted with dichloromethane (50 mL) and washed with water (50 mL) and brine (25 mL). The organic layer was dried over sodium sulfate, filtered and concentrated. The crude was purified by silica gel (220-400 mesh) column chromatography eluting with 5% methanol in dichloromethane. The desired fractions were concentrated under reduced pressure to afford 8'-chloro-6'-((2-methyl-2H-1,2,3-triazol-4-yl)amino)-2'H-spiro[cyclohexane-1,3'-imidazo[1,5-c]pyridine]-1',5'-dione (Cpd. No. 7) as a yellow solid. Yield: 0.1 g, 50%; MS (ESI) m/z 349.31[M+1]$^+$; $^1$H NMR (400 MHz, DMSO-$d_6$) δ 10.13 (s, 1H), 9.39 (s, 1H), 7.83 (s, 1H), 7.54 (s, 1H), 4.10 (s, 3H), 3.00-2.90 (m, 2H), 1.80-1.48 (m, 7H), 1.27-1.17 (m, 1H).

N,N'-dimethylcyclohexane 1,2-diamine (257 mg, 1.81 mmol) were added and the mixture was purged for another 5 min. The reaction mixture was stirred at 100° C. for 16 h. After completion, the reaction mass was diluted with dichloromethane (25 mL) and washed with water (25 mL) and brine (25 mL). The organic layer was dried over sodium sulfate, filtered and concentrated. The crude was purified by silica gel (220-400 mesh) column chromatography using 5% methanol in dichloromethane as eluent. The desired fractions were concentrated under reduced pressure to afford 8-chloro-6-(oxadiazol-5-ylamino)spiro[2H-imidazo[1,5-a]pyridine-3,1'-cyclohexane]-1,5-dione (Cpd. No. 8) as a brown solid. Yield: 0.007 g, 2%; MS (ESI) m/z 336.32[M+1]$^+$; $^1$H NMR (400 MHz, DMSO-$d_6$) δ 12.08 (s, 1H), 10.63 (s, 1H), 8.29 (s, 1H), 8.11 (s, 1H), 2.92-2.86 (m, 2H), 1.80-173 (m, 2H), 1.68-1.53 (m, 5H), 1.29-1.19 (m, 1H).

Example 8

Synthesis of 6'-((1,3,4-oxadiazol-2-yl)amino)-8'-chloro-2'H-spiro[cyclohexane-1,3'-imidazo[1,5-a]pyridine]-1',5'-dione (Cpd. No. 8)

Example 9

Synthesis of 6'-((2H-1,2,3-triazol-4-yl)amino)-8'-chloro-2'H-spiro[cyclohexane-1,3'-imidazo[1,5-a]pyridine]-1',5'-dione (Cpd. No. 9)

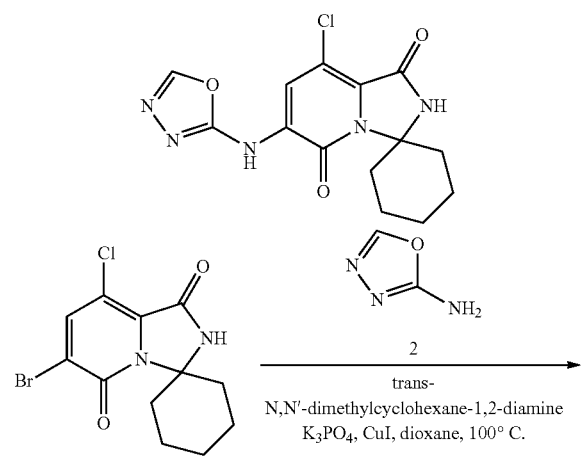

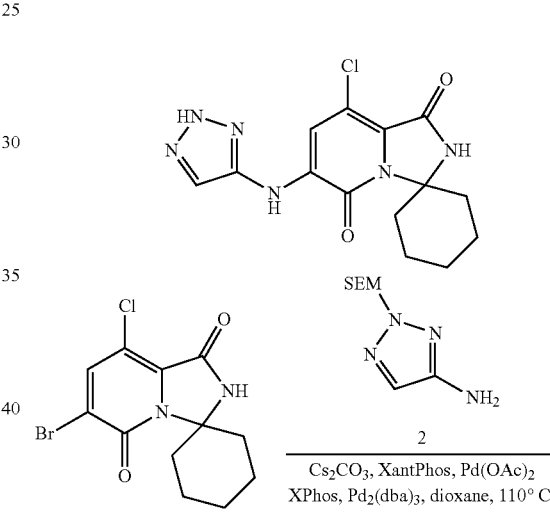

Synthesis of 6'-((1,3,4-oxadiazol-2-yl)amino)-8'-chloro-2'H-spiro[cyclohexane-1,3'-imidazo[1,5-a]pyridine]-1',5'-dione (Cpd. No. 8)

To a solution of 1,3,4-oxadiazol-2-amine (2, 0.38 g, 4.52 mmol) in dioxane (5 mL), 6-bromo-8-chloro-spiro[2H-imidazo[1,5-a]pyridine-3,1'-cyclohexane]-1,5-dione (1, 0.30 g, 0.90 mmol) and potassium phosphate (0.58 g, 2.71 mmol) were added. The reaction mixture was purged with argon for 10 min. Copper(I) iodide (17 mg, 0.090 mmol) and trans- Synthesis of 8'-chloro-6'-((2-((2-(trimethylsilyl)ethoxy)methyl)-2H-1,2,3-triazol-4-yl)amino)-2'H-spiro[cyclohexane-1,3'-imidazo[1,5-a]pyridine]-1',5'-dione (3)

To a solution of 2-((2-(trimethylsilyl)ethoxy)methyl)-2H-1,2,3-triazol-4-amine (2, 0.29 g, 1.36 mmol) in dioxane (25 mL), 6-bromo-8-chloro-spiro[2H-imidazo[1,5-a]pyridine-3,1'-cyclohexane]-1,5-dione (1, 0.3 g, 0.9 mmol) and cesium carbonate (0.88 g, 2.7 mmol) were added. The reaction mixture was purged with argon for 10 min. XantPhos (52 mg, 0.09 mmol), XPhos (42 mg, 0.09 mmol), tris(dibenzylideneacetone)dipalladium(0) (82 mg, 0.09 mmol) and palladium(II) acetate (20 mg, 0.09 mmol) were added and the mixture was purged for another 5 minutes. The reaction mixture was then stirred at 110° C. for 2 h. After completion, the reaction mass was diluted with dichloromethane (50 mL) and washed with water (50 mL) and brine (25 mL). The organic layer was dried over sodium sulfate, filtered and concentrated. The crude was purified by silica gel (220-400 mesh) column chromatography using 5% methanol in dichloromethane as eluent. The desired fractions were concentrated to afford 8'-chloro-6'-((2-((2-(trimethylsilyl)ethoxy)methyl)-2H-1,2,3-triazol-4-yl)amino)-2'H-spiro[cyclohexane-1,3'-imidazo[1,5-a]pyridine]-1',5'-dione (3) as an off-white solid. Yield: 0.3 g, 72%; MS (ESI) m/z 464.23 [M−1]⁻.

Synthesis of 6'-((2H-1,2,3-triazol-4-yl)amino)-8'-chloro-2'H-spiro[cyclohexane-1,3'-imidazo[1,5-a]pyridine]-1',5'-dione (Cpd. No. 9)

To a solution of 8'-chloro-6'-((2-((2-(trimethylsilyl)ethoxy)methyl)-2H-1,2,3-triazol-4-yl)amino)-2'H-spiro[cyclohexane-1,3'-imidazo[1,5-a]pyridine]-1',5'-dione (3, 0.3 g, 0.64 mmol) in dichloromethane (3 mL), trifluoroacetic acid (3 mL) was added at 0° C. The reaction mixture was stirred at ambient temperature for 16 h. After completion, the solvent was evaporated and the crude was purified by prep HPLC to afford 6'-((2H-1,2,3-triazol-4-yl)amino)-8'-chloro-2'H-spiro[cyclohexane-1,3'-imidazo[1,5-a]pyridine]-1',5'-dione (Cpd. No. 9) as a yellow solid. Yield: 0.022 g, 10%; MS (ESI) m/z 335.32[M+1]⁺; ¹H NMR (400 MHz, DMSO-d₆) δ 14.40 (s, 1H), 10.15 (s, 1H), 9.44 (s, 1H), 7.90 (s, 1H), 7.63 (s, 1H), 2.98-2.93 (m, 2H), 1.77-1.50 (m, 7H), 1.24-1.20 (m, 1H).

Example 10

Synthesis of 6'-((1,2,4-triazin-3-yl)amino)-8'-chloro-2'H-spiro[cyclohexane-1,3'-imidazo[1,5-a]pyridine]-1',5'-dione (Cpd. No. 10)

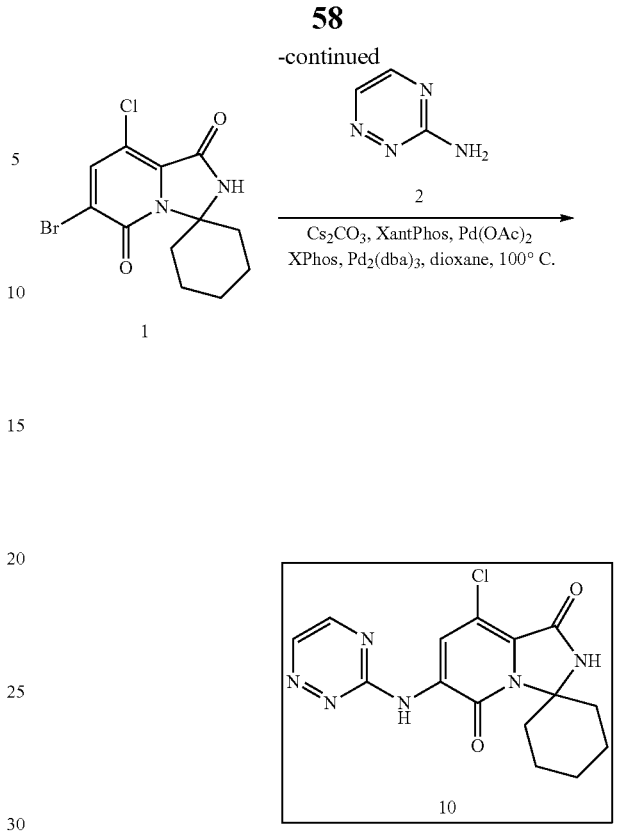

Synthesis of 6'-((1,2,4-triazin-3-yl)amino)-8'-chloro-2'H-spiro[cyclohexane-1,3'-imidazo[1,5-c]pyridine]-1',5'-dione (Cpd. No. 10)

To a solution of 1,2,4-triazin-3-amine (2, 0.14 g, 1.51 mmol) in dioxane (25 mL), 6-bromo-8-chloro-spiro[2H-imidazo[1,5-a]pyridine-3,1'-cyclohexane]-1,5-dione (1, 0.5 g, 1.51 mmol) and cesium carbonate (1.47 g, 4.53 mmol) were added. The reaction mixture was purged with argon for 10 min. XantPhos (44 mg, 0.075 mmol), XPhos (36 mg, 0.075 mmol), tris(dibenzylideneacetone)dipalladium(0) (69 mg, 0.075 mmol) and palladium(II) acetate (17 mg, 0.075 mmol) were added and the mixture was purged for another 5 min. The reaction mixture was stirred at 100° C. for 16 h. After completion, the reaction mass was diluted with dichloromethane (50 mL) and washed with water (50 mL) and brine (25 mL). The organic layer was dried over sodium sulfate, filtered and concentrated. The crude was purified by silica gel (220-400 mesh) column chromatography using 5% methanol in dichloromethane as eluent. The desired fractions were concentrated under reduced pressure to afford 6'-((1,2,4-triazin-3-yl)amino)-8'-chloro-2'H-spiro[cyclohexane-1,3'-imidazo[1,5-a]pyridine]-1',5'-dione (Cpd. No. 10) as a yellow solid. Yield: 0.30 g, 57%; MS (ESI) m/z 347.33[M+1]⁺; ¹H NMR (400 MHz, DMSO-d₆) δ 10.38 (brs, 1H), 9.05 (d, J=2.2 Hz, 1H), 8.81 (brs, 1H), 8.69 (d, J=2.2 Hz, 1H), 8.47 (s, 1H), 2.98-2.88 (m, 2H), 1.82-1.53 (m, 7H), 1.31-1.21 (m, 1H).

Example 11

Synthesis of 6'-((1,3,5-triazin-2-yl)amino)-8'-chloro-2'H-spiro[cyclohexane-1,3'-imidazo[1,5-a]pyridine]-1',5'-dione (Cpd. No. 11)

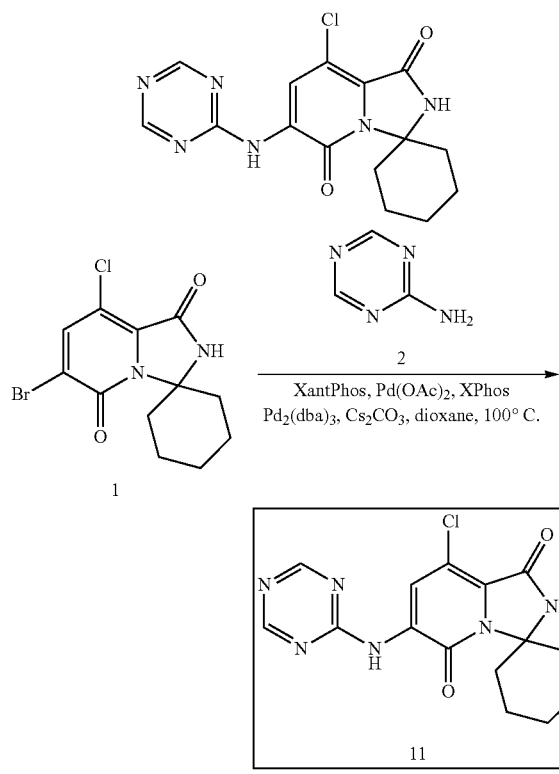

Example 12

Synthesis of 6'-((1,2,4-triazin-3-yl)amino)-8'-chloro-2'H-spiro[cyclohexane-1,3'-imidazo[1,5-a]pyridine]-1',5'-dione (Cpd. No. 12)

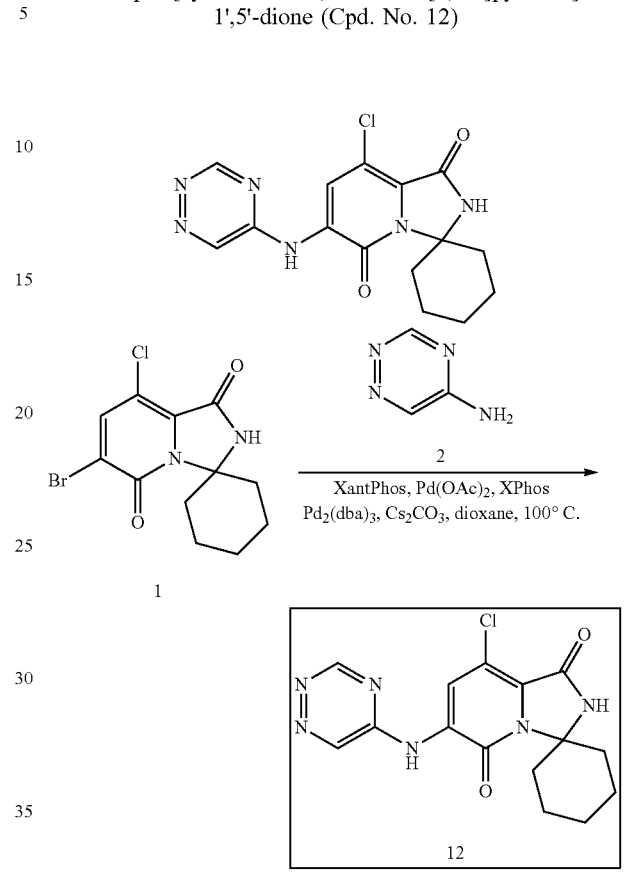

Synthesis of 6'-((1,3,5-triazin-2-yl)amino)-8'-chloro-2'H-spiro[cyclohexane-1,3'-imidazo[1,5-c]pyridine]-1',5'-dione (Cpd. No. 11)

A vial containing 1,4-dioxane (5 mL) was charged with 6'-bromo-8'-chloro-2'H-spiro[cyclohexane-1,3'-imidazo[1,5-a]pyridine]-1',5'-dione (1, 0.30 g, 0.90 mmol), 1,3,5-triazin-2-amine (2, 0.090 g, 0.90 mmol) and cesium carbonate (0.90 g, 2.71 mmol). The mixture was purged with argon for 10 min. XantPhos (0.026 g, 0.045 mmol), XPhos (0.021 g, 0.045 mmol), tris(dibenzylideneacetone)dipalladium(0) (0.041 g, 0.045 mmol) and palladium(II) acetate (0.010 g, 0.045 mmol) were added and the mixture was purged for another 5 min. The vial was sealed and the reaction mixture was heated at 100° C. for 2 h. After completion, the reaction mass was diluted with 5% methanol in dichloromethane (10 mL) and passed through a bed of alumina. The filtrate was concentrated under reduced pressure and purified by column chromatography using 2-5% methanol in dichloromethane. The desired fractions were concentrated to afford 6'-((1,3,5-triazin-2-yl)amino)-8'-chloro-2'H-spiro[cyclohexane-1,3'-imidazo[1,5-a]pyridine]-1',5'-dione (Cpd. No. 11) as a white solid. Yield: 0.15 g, 48%; MS (ESI) m/z: 347.24[M+1]$^+$; $^1$H NMR (400 MHz, trifluoroacetic acid-d$_1$) δ 9.14 (brs, 1H), 8.96 (s, 1H), 8.80 (s, 1H), 3.11-3.02 (m, 2H), 2.08-2.01 (m, 2H), 1.92-1.86 (m, 1H), 1.76-1.68 (m, 2H), 1.64-1.51 (m, 2H), 1.47-1.37 (m, 1H).

Synthesis of 8-chloro-6-(1,2,4-triazin-5-ylamino)spiro[2H-imidazo[1,5-a]pyridine-3,1'-cyclohexane]-1,5-dione (Cpd. No. 12)

In a vial, 1,2,4-triazin-5-amine (2, 0.09 g, 0.90 mmol) and 6-bromo-8-chloro-spiro[2H-imidazo[1,5-a]pyridine-3,1'-cyclohexane]-1,5-dione (1, 0.25 g, 0.75 mmol) were dissolved in 1,4-dioxane (5 mL). Cesium carbonate (0.61 g, 1.88 mmol) was added and the reaction mixture was purged with argon for 5 min. XantPhos (0.043 g, 0.074 mmol), palladium (II) acetate (0.017 g, 0.075 mmol), XPhos (0.036 g, 0.075 mmol) and tris(dibenzylideneacetone)dipalladium(0) (0.069 g, 0.075 mmol) were added and the mixture was purged for another 5 min. The vial was sealed and the reaction mixture was heated at 100° C. for 16 h. After completion, the reaction mixture was diluted with 5% methanol in dichloromethane and filtered over a bed of celite. The resulting filtrate was concentrated under reduced pressure and purified by flash column chromatography eluting with 2.5% methanol in dichloromethane. The desired fractions were separately concentrated to dryness under vacuum to afford 8-chloro-6-(1,2,4-triazin-5-ylamino)spiro[2H-imidazo[1,5-a]pyridine-3,1'-cyclohexane]-1,5-dione (Cpd. No. 12) as a yellow solid. Yield: 0.058 g, 22%; MS (ESI) m/z 347.27 [M+1]$^+$; $^1$H NMR (400 MHz, DMSO-d$_6$) δ 10.41 (brs, 1H), 10.19 (brs, 1H), 9.38 (s, 1H), 9.15 (s, 1H), 8.72 (s, 1H), 3.00-2.88 (m, 2H), 1.75-154 (m, 7H), 1.27-1.17 (m, 1H).

Example 13

Synthesis of 6'-((2-aminopyridin-4-yl)amino)-8'-chloro-2'H-spiro[cyclohexane-1,3'-imidazo[1,5-a]pyridine]-1',5'-dione (Cpd. No. 13)

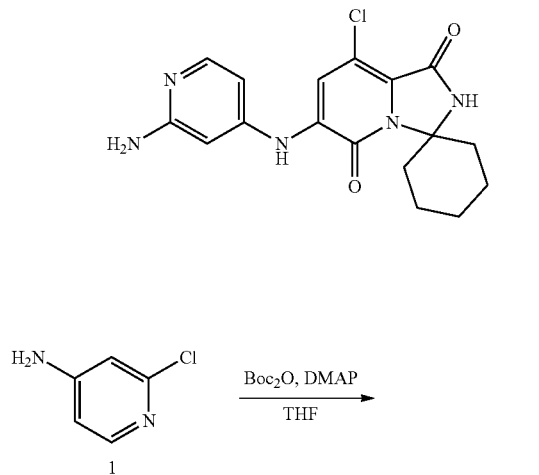

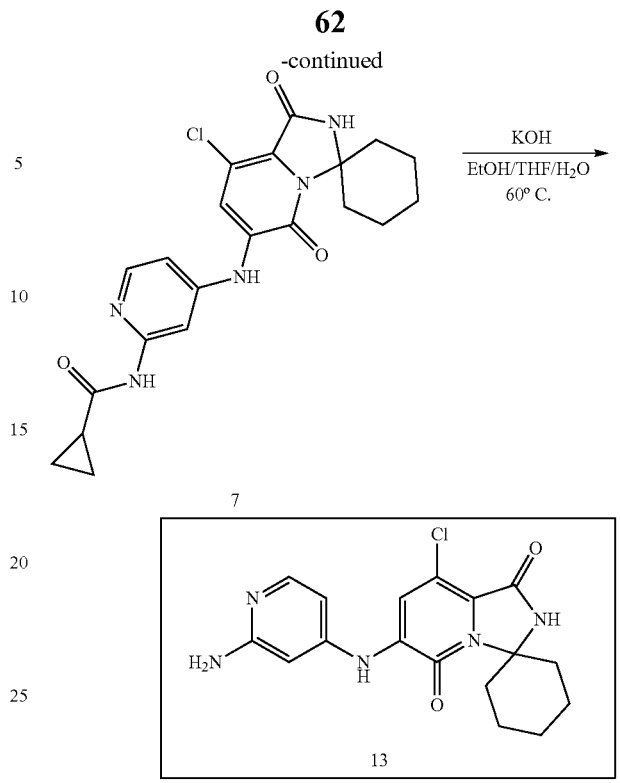

Synthesis of tert-butyl-tert-butoxycarbonyl(2-chloropyridin-4-yl)carbamate (2)

To a solution of 2-chloropyridin-4-amine (1, 1.0 g, 15.56 mmol) in tetrahydrofuran (25 mL), di-tert-butyl dicarbonate (16.98 g, 77.79 mmol) and 4-dimethylaminopyridine (0.19 g, 1.56 mmol) were added. The reaction mixture was stirred at room temperature for 48 h. After completion, the mixture was quenched with ice water and extracted with ethyl acetate. The organic layer was washed with water and brine, dried over anhydrous sodium sulfate, filtered and concentrated to get tert-butyl-tert-butoxycarbonyl(2-chloropyridin-4-yl)carbamate (2) as an off-white solid. Yield: 1.40 g, 27%; MS (ESI) m/z 329.17[M+1]$^+$.

Synthesis of tert-butyl (2-(cyclopropanecarboxamido)pyridin-4-yl)carbamate (4)

A vial containing 1,4-dioxane (15 mL) was charged with tert-butyl-tert-butoxycarbonyl(2-chloropyridin-4-yl)carbamate (2, 1.0 g, 3.04 mmol), cyclopropanecarboxamide (3, 0.31 g, 3.65 mmol) and cesium carbonate (2.97 g, 9.12 mmol). The mixture was purged with argon for 15 min. XantPhos (0.088 g, 0.152 mmol) and palladium(II) acetate (0.034 g, 0.152 mmol) were added and the mixture was purged for another 5 min. The vial was sealed and the reaction mixture was heated at 90° C. for 16 h. After completion, the reaction mixture was passed through a celite pad. The filtrate was concentrated under reduced pressure and washed with pentane and ether to afford tert-butyl-tert-butoxycarbonyl(2-(cyclopropanecarboxamido)pyridin-4-yl)carbamate (4) as a light yellow solid. Yield: 1.6 g, crude; MS (ESI) m/z 378.3[M+1]$^+$.

Synthesis of N-(4-aminopyridin-2-yl)cyclopropanecarboxamide (5)

A solution of tert-butyl (2-(cyclopropanecarboxamido)pyridin-4-yl)carbamate (4, 1.6 g, 4.24 mmol) in dichloromethane (5 mL) was treated with trifluoroacetic acid (5 mL) at 0° C. and the reaction mixture was stirred at room temperature for 16 h. After completion, the solvent was removed under reduced pressure. The residue was diluted with ammonium hydroxide solution and extracted with 5% methanol in dichloromethane. The organic layer was washed with water and brine, dried over anhydrous sodium sulfate, filtered and concentrated. The solid was washed with ether, pentane and dried under vacuum to afford N-(4-aminopyridin-2-yl)cyclopropanecarboxamide (5) as an off-white solid. Yield: 1.1 g, 100%; MS (ESI) m/z 178.2[M+1]$^+$.

Synthesis of N-(4-((8'-chloro-1',5'-dioxo-1',5'-dihydro-2'H-spiro[cyclohexane-1,3'-imidazo[1,5-a]pyridin]-6'-yl)amino)pyridin-2-yl)cyclopropanecarboxamide (7)

To a solution of 6-bromo-8-chloro-spiro[2H-imidazo[1,5-a]pyridine-3,1'-cyclohexane]-1,5-dione (6, 0.5 g, 1.51 mmol) and N-(4-aminopyridin-2-yl)cyclopropanecarboxamide (5, 0.267 g, 1.51 mmol) in dioxane (12 mL), cesium carbonate (0.589 g, 1.81 mmol) was added. The reaction mixture was purged with argon for 20 min. XantPhos (43 mg, 0.07 mmol), XPhos (36 mg, 0.07 mmol), tris(dibenzylideneacetone)dipalladium(0) (69 mg, 0.07 mmol) and palladium(II) acetate (17 mg, 0.07 mmol) were added and the mixture was purged for another 10 min. The reaction mixture was stirred at 90° C. for 16 h. After completion, the reaction mass was diluted with 5% methanol in dichloromethane and passed through a celite pad. The filtrate was concentrated under reduced pressure and the crude was purified by silica gel (230-400 mesh) column chromatography eluting with 2-3% methanol in dichloromethane. Appropriate column fractions were concentrated to afford N-(4-((8'-chloro-1',5'-dioxo-1',5'-dihydro-2'H-spiro[cyclohexane-1,3'-imidazo[1,5-a]pyridin]-6'-yl)amino)pyridin-2-yl)cyclopropanecarboxamide (7) as a yellow solid. Yield: 0.1 g, 16%; MS (ESI) m/z 426.49 [M−1]$^−$.

Synthesis of 6'-((2-aminopyridin-4-yl)amino)-8'-chloro-2'H-spiro[cyclohexane-1,3'-imidazo[1,5-a]pyridine]-1',5'-dione (Cpd. No. 13)

N-(4-((8'-Chloro-1',5'-dioxo-1',5'-dihydro-2'H-spiro[cyclohexane-1,3'-imidazo[1,5-a]pyridin]-6'-yl)amino)pyridin-2-yl)cyclopropanecarboxamide (7, 0.10 g, 0.235 mmol) was dissolved in a mixture of tetrahydrofuran, ethanol, and water (2.5 mL each). Potassium hydroxide (0.13 g, 2.35 mmol) was added and the reaction mixture was heated at 60° C. for 72 h. After completion, the solvent was removed under reduced pressure before ethyl acetate and water were added. The organic layer was washed with brine, dried over anhydrous sodium sulfate, filtered and concentrated. The crude was purified by column chromatography eluting with 2-3% methanol in dichloromethane. Appropriate column fractions were concentrated under reduced pressure to afford 6'-((2-aminopyridin-4-yl)amino)-8'-chloro-2'H-spiro[cyclohexane-1,3'-imidazo[1,5-a]pyridine]-1',5'-dione (Cpd. No. 13) as a yellow solid. Yield: 0.045 g, 54%; MS (ESI) m/z 360.29[M+1]$^+$; $^1$H NMR (400 MHz, DMSO-d$_6$) δ 10.19 (s, 1H), 8.42 (s, 1H), 7.75 (d, J=5.2 Hz, 1H), 7.14 (s, 1H), 6.49 (d, J=5.0 Hz, 1H), 6.39 (s, 1H), 5.86 (s, 2H), 2.96-2.90 (m, 2H), 1.82-1.50 (m, 7H), 1.23-1.20 (m, 1H).

Example 14: MNK Biochemical Enzymatic Assay

Compounds are screened for MNK inhibition using the ADP-Glo kinase assay kit (Promega, catalogue No. V9101).

All kinase reactions are performed in Reaction Buffer E (15 mM HEPES pH7.4, 20 mM NaCl, 1 mM EGTA, 10 mM MgCl$_2$, 0.1 mg/ml BGG, and 0.02% Tween-20). Final MNK1 reactions contained 10 nM recombinant MNK1 (Life Technologies, PR9138A), 100 μM MNK substrate peptide Ac-TATKSGSTTKNR-NH2 (American Peptide Company), 300 μM ATP, and varying concentrations of the inhibitory compound of interest. Final MNK2 reactions contained 3 nM recombinant MNK2 (Life Technologies, PV5607), 50 μM MNK substrate peptide Ac-TATKSGSTTKNR-NH2 (American Peptide Company), 10 μM ATP, and varying concentrations of the inhibitory compound of interest. Final DMSO concentration in each reaction is 1%.

Kinase reactions are carried out in 96-well half-area white flat-bottom polystyrene plates in a final volume of 25 μl. MNK1/2 enzymes are pre-incubated with compound and peptide substrate for 5 minutes prior to the addition of ATP. After the addition of ATP, kinase reactions are incubated at room temperature for 40 minutes. Reactions are subsequently stopped by the addition of 25 μl of ADP-Glo Reagent and incubating for an additional 40 minutes. The final luminescent signal used for kinase activity readout is produced by the addition of 45 μl of Kinase Detection Reagent (ADP-Glo kit, Promega) and incubating for 40 minutes. The luminescent signal is detected using a Victor 2 multilabel counter (Perkin Elmer) and the concentration of compound necessary to achieve inhibition of enzyme activity by 50% (IC$_{50}$) is calculated using signals from an 8-point compound dilution series.

The results of this assay are set forth in Table 1 below. To this end, IC$_{50}$ values of less than 0.01 μM are labelled as "+++", from 0.01 to 0.10 μM are labelled as "++", from 0.1 to 10 μM are labelled as "+", greater than 10 μM are labelled inactive, and NA means "not available".

Example 15: peIF4E Signaling Cellular Assay

Phosphorylated eIF4E is assayed using the CisBio peIF4E HTRF® assay kit (CisBio, catalogue No. 64EF4PEG). Cells are plated in 96-well tissue-culture treated plate in appropriate growth medium (90 μL). Compounds (10×) are diluted using 3-fold serial dilutions in cell culture medium and added to cells. Plates are incubated for 2 hrs at 37° C. The cell supernatant is carefully removed either by aspirating supernatant or by flicking the plate. Immediately 50 μL of supplemented lysis buffer (1×) is added and incubated for at least 30 minutes at room temperature under shaking. After homogenization by pipeting up and down, 16 μL of cell lysate is transferred from the 96-well cell-culture plate to a 384-well small volume white plate. 4 μL of premixed antibody solutions (vol/vol) is prepared in the detection buffer and added. The plate is covered with a plate sealer and incubated overnight at room temperature. The fluorescence emissions at two different wavelengths are read (665 nm and 620 nm) on a Wallac Victor2. Emission ratios are converted into percent inhibitions and imported into GraphPad Prism software. The concentration of compound necessary to achieve inhibition of enzyme activity by 50% (IC$_{50}$) is calculated using concentrations ranging from 20 μM to 0.1 nM (12-point curve). IC$_{50}$ values are determined using a nonlinear regression model available in GraphPad Prism 5.

The results of this assay are set forth in Table 1 below. To this end, IC$_{50}$ values of less than 0.01 μM are labelled as "+++", from 0.01 to 0.10 μM are labelled as "++", from 0.10 to 100 μM are labelled as "+", greater than 100 μM are labelled inactive, and NA means "not available".

TABLE 1

| EXAMPLE | STRUCTURE | MNK1 IC$_{50}$ | MNK2 IC$_{50}$ | peIF4E Cellular IC$_{50}$ |
|---|---|---|---|---|
| 1F | 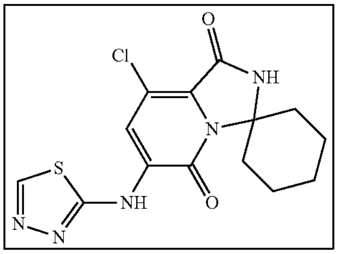 | + | ++ | + |
| 2F | 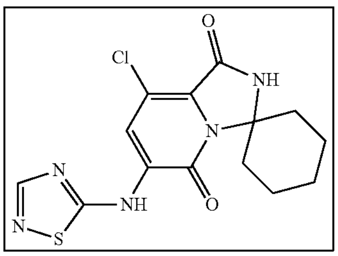 [SMILES: O=C1NC2(CCCCC2)n2c1c(Cl)cc(Nc1ncns1)c2=O] | ++ | +++ | + |
| 3 | 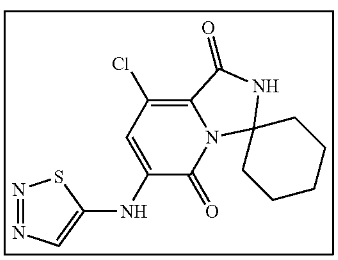 [SMILES: O=C1NC2(CCCCC2)n2c1c(Cl)cc(Nc1cnns1)c2=O] | Inactive | ++ | + |
| 4F | 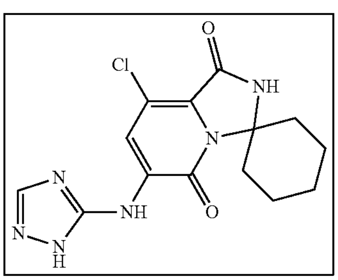 [SMILES: O=C1NC2(CCCCC2)n2c1c(Cl)cc(Nc1ncn[nH]1)c2=O] | + | ++ | NA |
| 5 | 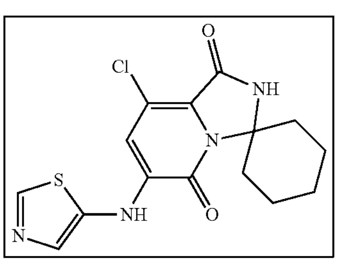 [SMILES: O=C1NC2(CCCCC2)n2c1c(Cl)cc(Nc1cncs1)c2=O] | + | ++ | NA |

TABLE 1-continued

| EXAMPLE | STRUCTURE | MNK1 IC$_{50}$ | MNK2 IC$_{50}$ | peIF4E Cellular IC$_{50}$ |
|---|---|---|---|---|
| 6 | 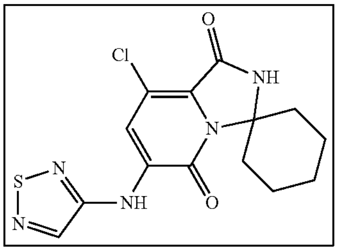 [SMILES: O=C1NC2(CCCCC2)n2c1c(Cl)cc(Nc1cnsn1)c2=O] | NA | +++ | + |
| 7 | 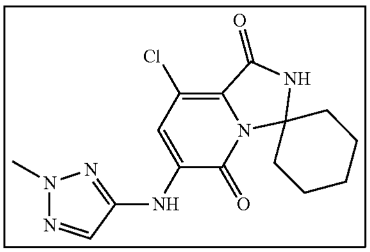 [SMILES: Cn1ncc(Nc2cc(Cl)c3n(c2=O)C2(CCCCC2)NC3=O)n1] | NA | +++ | + |
| 8 | 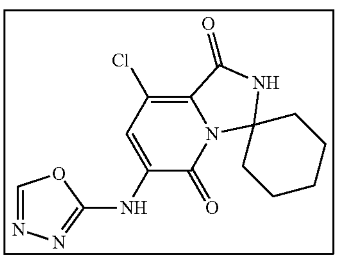 [SMILES: O=C1NC2(CCCCC2)n2c1c(Cl)cc(Nc1nnco1)c2=O] | + | + | + |
| 9 | 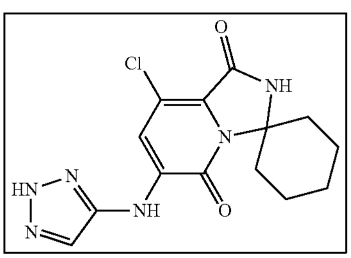 [SMILES: O=C1NC2(CCCCC2)n2c1c(Cl)cc(Nc1cn[nH]n1)c2=O] | ++ | +++ | + |
| 10 | 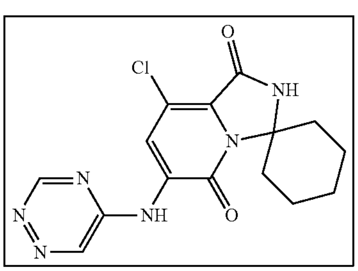 [SMILES: O=C1NC2(CCCCC2)n2c1c(Cl)cc(Nc1cnncn1)c2=O] | NA | ++ | + |

TABLE 1-continued

| EXAMPLE | STRUCTURE | MNK1 IC$_{50}$ | MNK2 IC$_{50}$ | peIF4E Cellular IC$_{50}$ |
|---|---|---|---|---|
| 11 | 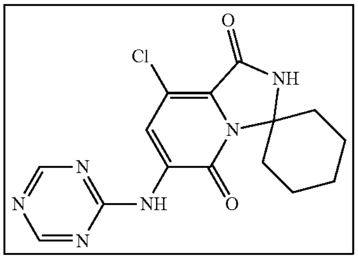 [SMILES: O=C1NC2(CCCCC2)n2c1c(Cl)cc(Nc1ncncn1)c2=O] | NA | +++ | ++ |
| 12 | 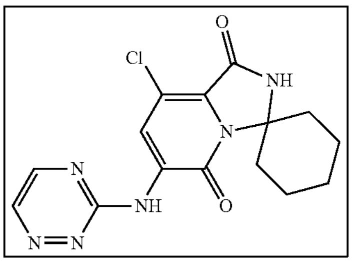 [SMILES: O=C1NC2(CCCCC2)n2c1c(Cl)cc(Nc1nccnn1)c2=O] | Inactive | ++ | NA |
| 13 | 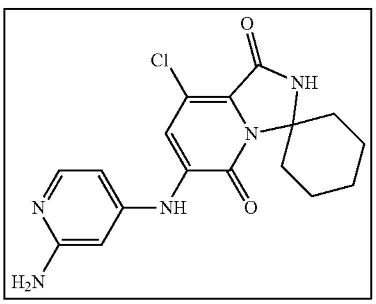 [SMILES: Nc1cc(Nc2cc(Cl)c3n(c2=O)C2(CCCCC2)NC3=O)ccn1] | NA | ++ | + |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A compound according to Formula IA,

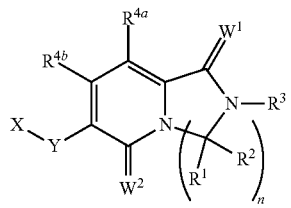

(IA)

or a stereoisomer, a tautomer or a pharmaceutically acceptable salt thereof wherein:

$W^1$ and $W^2$ each are O;

Y is —$NR^8$;

n is 1;

$R^1$ and $R^2$ independently are H, ($C_1$-$C_8$)alkyl, ($C_2$-$C_8$) alkenyl, ($C_2$-$C_8$)alkynyl, cycloalkyl, heterocyclyl, heteroaryl, aryl, arylalkylene, cycloalkylalkylene, heterocyclylalkylene or heteroarylalkylene; or $R^1$ and $R^2$ together with the carbon atom to which they are attached form a cycloalkyl or heterocyclyl ring;

$R^3$ is hydrogen or lower alkyl;

$R^{4a}$ is hydrogen, halogen, or ($C_1$-$C_8$)alkyl;

$R^{4b}$ is hydrogen;

$R^8$ is —H;

X is selected from the following table:

| 71 | 72 |
|---|---|
| | -continued |
| 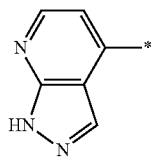 | 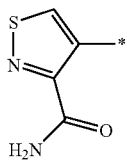 |
| 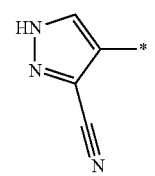 | 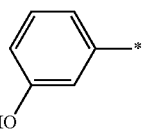 |
| 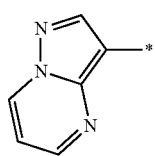 [SMILES: *c1cnn2cccnc12] | 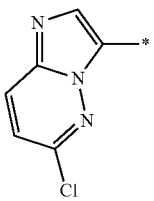 |
| 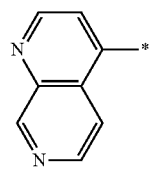 [SMILES: *c1ccnc2cnccc12] | 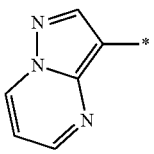 |
| 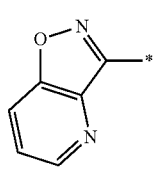 [SMILES: *c1noc2cccnc12] | 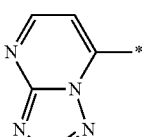 |
| 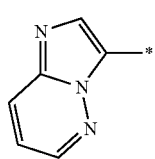 [SMILES: *c1cnc2cccnn12] | 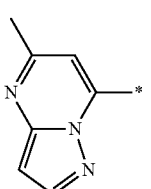 |
| 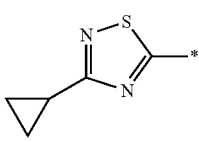 [SMILES: *c1nc(C2CC2)ns1] | 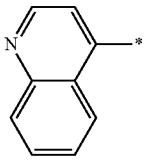 |
| 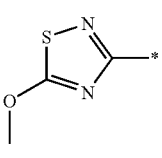 [SMILES: *c1nsc(OC)n1] | 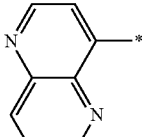 |
| 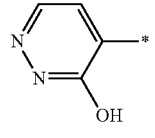 | 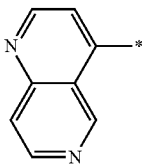 |
| 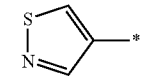 | |

73
-continued
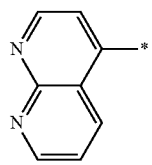 [SMILES: *c1ccnc2ncccc12]
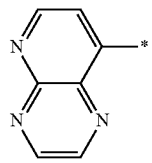 [SMILES: *c1ccnc2nccnc12]
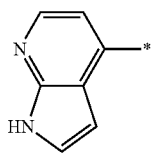 [SMILES: *c1ccnc2[nH]ccc12]
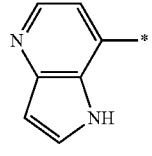 [SMILES: *c1ccnc2cc[nH]c12]
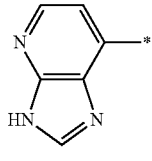 [SMILES: *c1ccnc2[nH]cnc12]
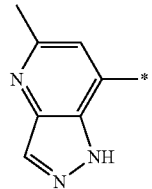 [SMILES: *c1cc(C)nc2cn[nH]c12]
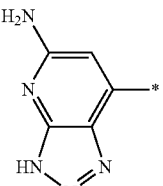
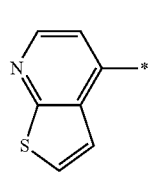
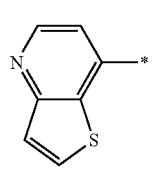 [SMILES: *c1ccnc2ccsc12]
74
-continued
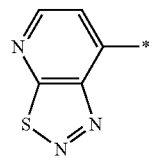 [SMILES: *c1ccnc2snnc12]
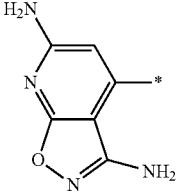 [SMILES: *c1cc(N)nc2onc(N)c12]
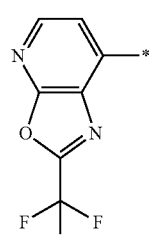
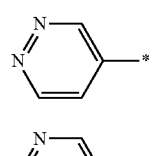
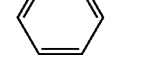
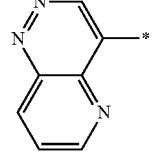
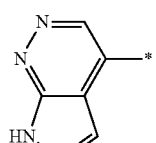
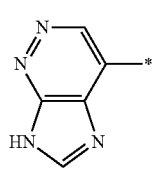 [SMILES: *c1cnnc2[nH]cnc12]
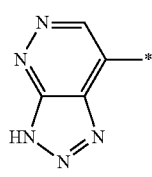

75
-continued
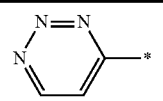
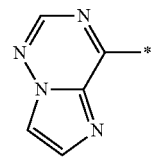 [SMILES: *c1ncnn2ccnc12]
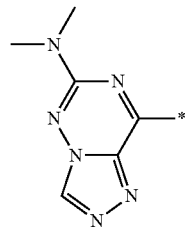 [SMILES: *c1nc(N(C)C)nn2cnnc12]
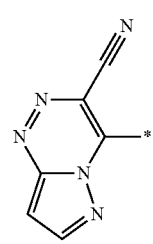 [SMILES: *c1c(C#N)nnc2ccnn12]
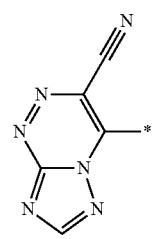 [SMILES: *c1c(C#N)nnc2ncnn12]
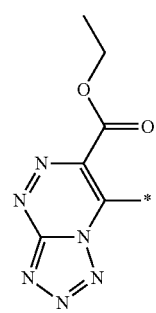 [SMILES: *c1c(C(=O)OCC)nnc2nnnn12]
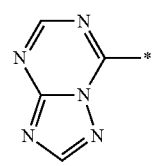
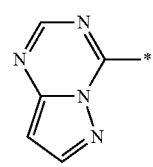
76
-continued
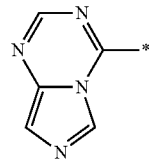 [SMILES: *c1ncnc2cncn12]
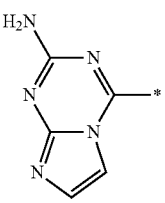
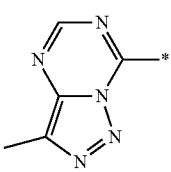
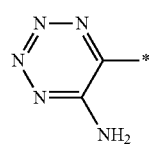
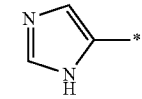
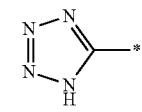 [SMILES: *c1nnn[nH]1]
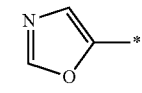
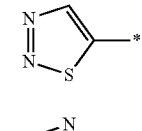
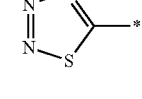
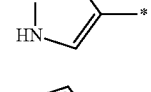
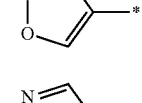
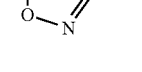

-continued
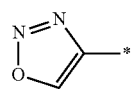
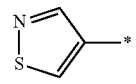 [SMILES: *c1cnsc1]
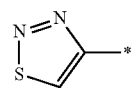
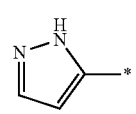
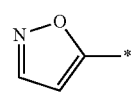 [SMILES: *c1ccno1]
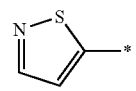 [SMILES: *c1ccns1]
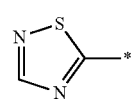 [SMILES: *c1ncns1]
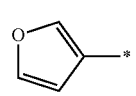 [SMILES: *c1ccoc1]
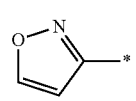 [SMILES: *c1ccon1]
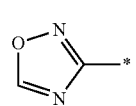 [SMILES: *c1ncon1]
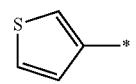 [SMILES: *c1ccsc1]
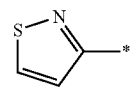
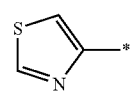
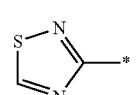
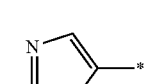
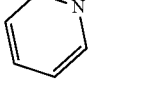
-continued
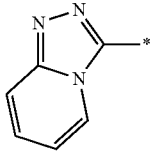 [SMILES: *c1nnc2ccccn12]
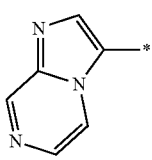 [SMILES: *c1cnc2cnccn12]
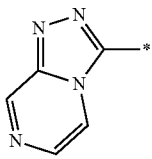 [SMILES: *c1nnc2cnccn12]
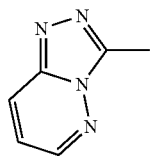
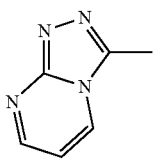
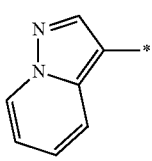 [SMILES: *c1cnn2ccccc12]
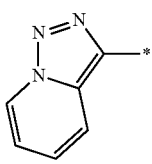 [SMILES: *c1nnn2ccccc12]
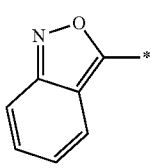 [SMILES: *c1onc2ccccc12]

| 79 -continued | | 80 -continued |
|---|---|---|
| 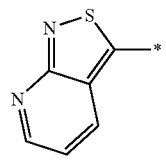 | 5 | 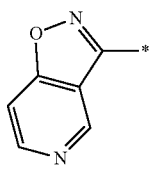 |
| 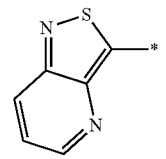 [SMILES: *c1snc2cccnc12] | 10 15 | 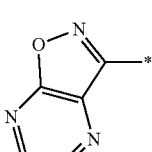 |
| 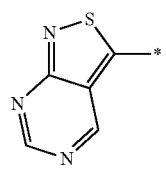 [SMILES: *c1snc2ncncc12] | 20 | 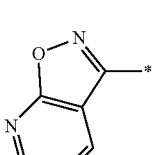 |
| 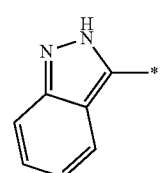 | 25 30 | 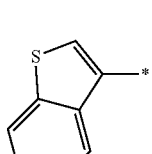 |
| 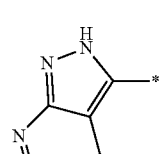 | 35 | 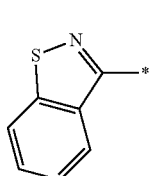 |
| 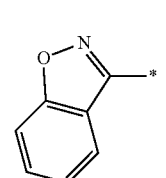 | 40 45 | 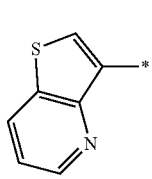 |
| 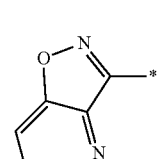 | 50 | 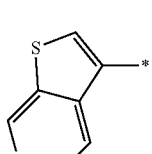 |
| 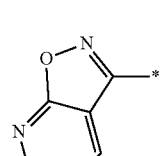 | 55 | 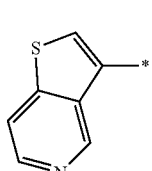 |
| 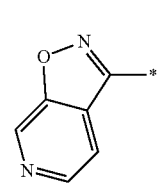 [SMILES: *c1noc2cnccc12] | 60 65 | 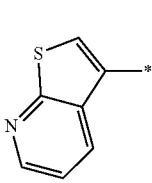 [SMILES: *c1csc2ncccc12] |

-continued
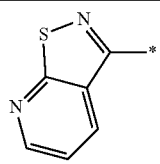
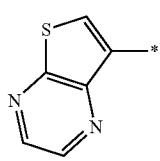 [SMILES: *c1csc2nccnc12]
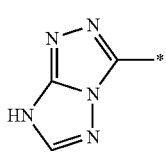
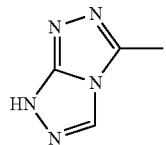
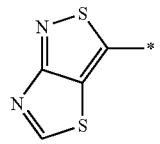 [SMILES: *c1snc2ncsc12]
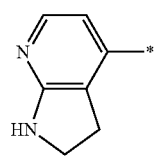 [SMILES: *c1ccnc2c1CCN2]
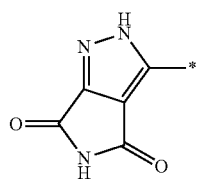 [SMILES: *c1[nH]nc2c1C(=O)NC2=O]
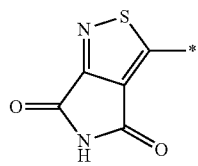 [SMILES: *c1snc2c1C(=O)NC2=O]
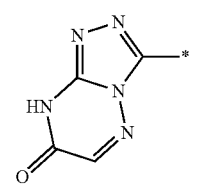
-continued
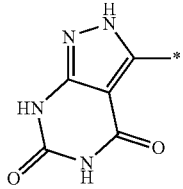 [SMILES: *c1[nH]nc2[nH]c(=O)[nH]c(=O)c12]
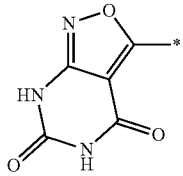 [SMILES: *c1onc2[nH]c(=O)[nH]c(=O)c12]
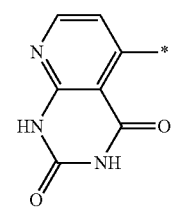 [SMILES: *c1ccnc2[nH]c(=O)[nH]c(=O)c12]
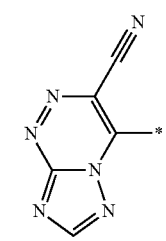 [SMILES: *c1c(C#N)nnc2ncnn12]
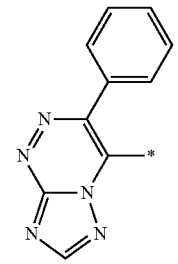 [SMILES: *c1c(-c2ccccc2)nnc2ncnn12]
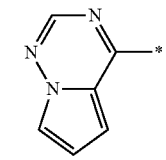
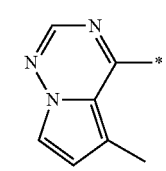 [SMILES: *c1ncnn2ccc(C)c12]
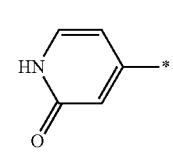

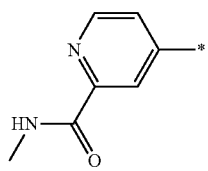 [SMILES: *c1ccnc(C(=O)NC)c1]

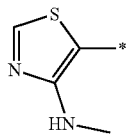

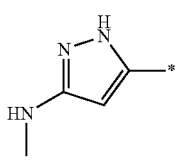

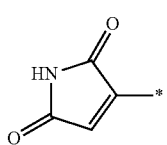 [SMILES: *C1=CC(=O)NC1=O]

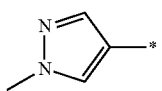 [SMILES: *c1cnn(C)c1]

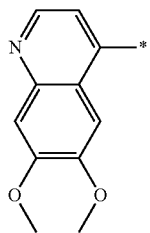 [SMILES: *c1ccnc2cc(OC)c(OC)cc12]

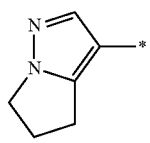 [SMILES: *c1cnn2c1CCC2]

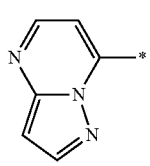

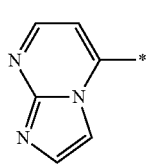

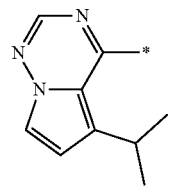 [SMILES: *c1ncnn2ccc(C(C)C)c12]

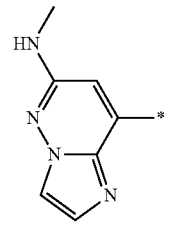

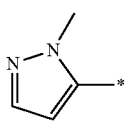

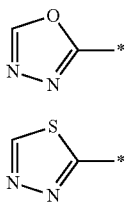

wherein * indicates the point of attachment of variable "X" to variable "Y"; and wherein any alkyl, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl is optionally substituted with 1, 2, or 3 groups selected from —OH, —CN, —SH, —S(O)NH$_2$, —S(O)NH$_2$, halogen, —NH$_2$, oxo, —NH(C$_1$-C$_4$)alkyl, —N[(C$_1$-C$_4$)alkyl]$_2$, —C(O)NH$_2$, —COOH, —COOMe, acetyl, —(C$_1$-C$_8$)alkyl, —O(C$_1$-C$_8$)alkyl (C$_2$-C$_8$)alkenyl, (C$_2$-C$_8$)alkynyl, haloalkyl, thioalkyl, cyanomethylene, alkylaminyl, NH$_2$—C(O)-alkylene, NH$_2$—C(O)-alkylene, —NH(Me)-C(O)-alkylene, —CH$_2$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$_2$—C(O)-cycloalkyl, —C(O)-cycloalkyl, —CH$_2$—C(O)-aryl, —CH$_2$-aryl, —C(O)-aryl, —CH$_2$—C(O)-heterocycloalkyl, —C(O)-heterocycloalkyl, heterocyclylaminyl or heterocyclyl.

2. The compound according to claim 1 wherein at least one of R$^1$ or R$^2$ is a halogen substituted (C$_1$-C$_8$)alkyl, cycloalkyl, heterocyclyl, heteroaryl, aryl, arylalkylene, cycloalkylalkylene, heterocyclylalkylene or heteroaryl alkylene.

3. The compound according to claim 1 wherein R$^1$ and R$^2$ together with the respective carbon atom to which they are attached form a cycloalkyl that is selected from cyclobutyl, cyclopentyl, cyclohexyl, 2,2-dimethylcyclobutyl, 4-aminocyclohexyl, 4-methylcyclohexyl, 4-ethylcyclohexyl, 2,2-difluoroethyl-4-cyclohexyl, 4,4-difluorocyclohexyl, 4-cyanocyclohexyl, 4-trifluoromethylcyclohexyl, 4-hydroxycyclohexyl, 3-hydroxycyclopentyl, 3-aminocyclopentyl and 3-methylcyclopentyl.

4. The compound according to claim 1 selected from

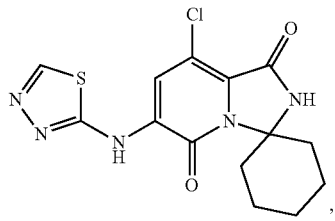

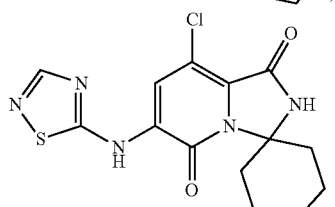

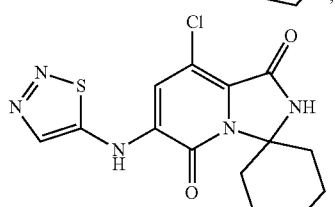

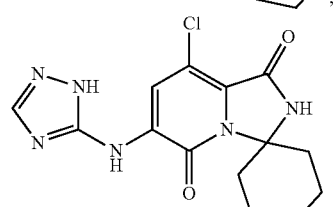

4F

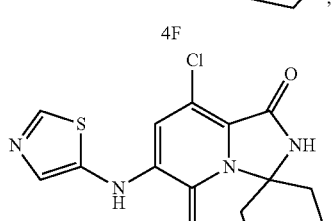

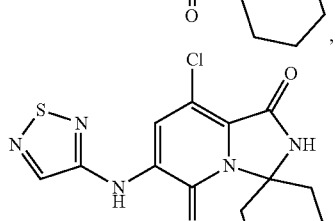

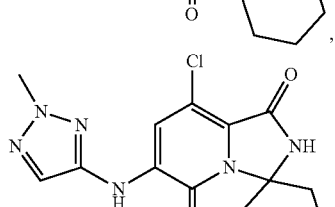

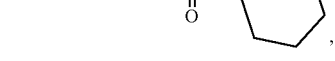

-continued

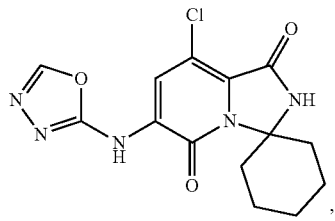

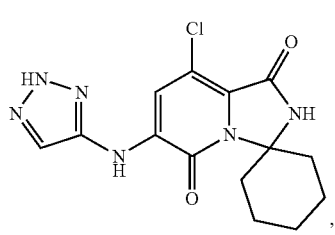

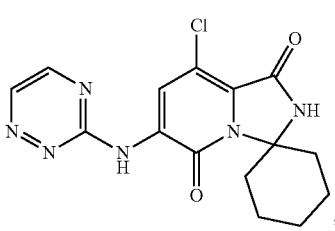

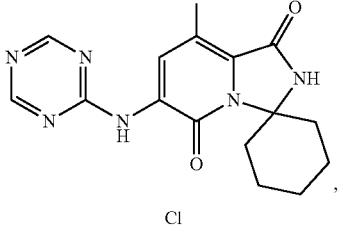

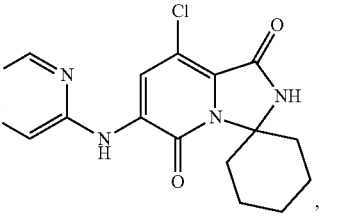

, and

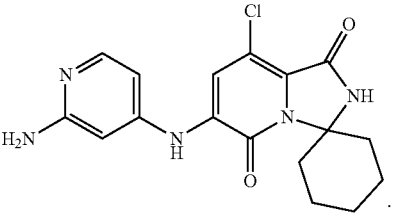

.

5. A pharmaceutical composition comprising (i) a therapeutically effective amount of at least one compound according to claim 1 or a stereoisomer, a tautomer or a pharmaceutically acceptable salt thereof; (ii) in combination with a pharmaceutically acceptable carrier, diluent or excipient.

* * * * *